United States Patent
Gaffney et al.

(10) Patent No.: US 10,759,907 B2
(45) Date of Patent: Sep. 1, 2020

(54) DEFINED MONOMER SEQUENCE POLYMERS

(71) Applicant: IP2IPO Innovations Limited, London (GB)

(72) Inventors: Piers Gaffney, London (GB); Andrew Livingston, London (GB); Rongjun Chen, London (GB); Ruijiao Dong, London (GB); Ruiyi Liu, London (GB); Patrizia Marchetti, London (GB)

(73) Assignee: IP2IPO INNOVATIONS LIMITED, London (GB)

( * ) Notice: Subject to any disclaimer, the term of this patent is extended or adjusted under 35 U.S.C. 154(b) by 0 days.

(21) Appl. No.: 15/758,162

(22) PCT Filed: Sep. 9, 2016

(86) PCT No.: PCT/GB2016/052801
§ 371 (c)(1),
(2) Date: Mar. 7, 2018

(87) PCT Pub. No.: WO2017/042583
PCT Pub. Date: Mar. 16, 2017

(65) Prior Publication Data
US 2018/0244845 A1   Aug. 30, 2018

(30) Foreign Application Priority Data
Sep. 10, 2015   (GB) .................................. 1516067.4

(51) Int. Cl.
*C08G 65/333* (2006.01)
*C08G 65/32* (2006.01)
(Continued)

(52) U.S. Cl.
CPC ........ *C08G 65/33396* (2013.01); *A61K 47/60* (2017.08); *A61K 49/0054* (2013.01);
(Continued)

(58) Field of Classification Search
CPC .... C08G 65/32; C08G 65/325; C08G 65/333; C08G 65/3344; C08G 65/3348;
(Continued)

(56) References Cited

U.S. PATENT DOCUMENTS 10,239,996 B2 * 3/2019 Shaepertoens ......... C08G 65/30

FOREIGN PATENT DOCUMENTS

WO   2010/015864 A1   2/2010
WO   2011/148177 A2   12/2011
(Continued)

OTHER PUBLICATIONS

International Search Report and Written Opinion for Application No. PCT/GB2016/052801, dated Dec. 6, 2016. 10 pages.
(Continued)

*Primary Examiner* — Shane Fang
(74) *Attorney, Agent, or Firm* — McCarter & English, LLP; Steven G. Davis; Wei Song

(57) ABSTRACT

Processes of preparing defined monomer sequence polymers are disclosed, in which a backbone portion of the polymer is first prepared by performing one or more sequential monomeric coupling reactions with intervening membrane diafiltration purification/isolation steps, followed by a step of decorating the backbone portion with one or more side chains at predetermined positions along its length. The process represents an improvement on prior art techniques, which impose limitations on the size of the side chains that may be present. Defined monomer sequence polymers that are obtainable by the processes are also disclosed.

17 Claims, 23 Drawing Sheets

(51) Int. Cl.
  *C08G 65/325* (2006.01)
  *A61K 47/60* (2017.01)
  *A61K 49/00* (2006.01)
  *A61K 49/12* (2006.01)
  *C08G 65/334* (2006.01)

(52) U.S. Cl.
  CPC ............ *A61K 49/128* (2013.01); *C08G 65/32* (2013.01); *C08G 65/325* (2013.01); *C08G 65/333* (2013.01); *C08G 65/3342* (2013.01); *C08G 65/3344* (2013.01); *C08G 65/3348* (2013.01); *C08G 65/33317* (2013.01)

(58) Field of Classification Search
  CPC ........ C08G 65/33396; C08G 65/33317; C08G 65/3342; A61K 47/60; A61K 49/128; A61K 49/0054
  See application file for complete search history.

(56) References Cited

FOREIGN PATENT DOCUMENTS

| WO | 2015/054669 A1 | 4/2015 |
| WO | 2016/020696 A1 | 2/2016 |
| WO | 2016/020708 A1 | 2/2016 |

OTHER PUBLICATIONS

Combined Search and Examination Report for Application No. GB1516067.4, dated Mar. 9, 2016. 6 pages.

\* cited by examiner

Functional side-chain table

1) Targeting molecules
2) Drugs
3) Imaging agents

4) Sugars

5) Amino acids, peptides

6) Nucleobases, aptamers, oligonucleotides

7) Monodisperse synthetic polymers

US 10,759,907 B2

DEFINED MONOMER SEQUENCE POLYMERS

CROSS-REFERENCE TO RELATED APPLICATIONS

This application is a U.S. national stage filing, under 35 U.S.C. § 371(c), of International Application No. PCT/GB2016/052801, filed on Sep. 9, 2016, which claims priority to United Kingdom Application No. 1516067.4, filed on Sep. 10, 2015. The entire contents of each of the aforementioned applications are incorporated herein by reference.

INTRODUCTION

The present invention relates to the preparation of defined monomer sequence polymers. In particular, the present invention relates to the preparation of defined monomer sequence polymers by diafiltration processes. The present invention also relates to defined monomer sequence polymers obtainable by the described processes.

BACKGROUND OF THE INVENTION

The primary structure of polymeric materials—that is, the sequential arrangement of monomer units in a polymer chain—is generally poorly controlled in synthetic macromolecules. Common polymers are usually homopolymers, made of the same monomer unit, or copolymers with simple chain microstructures, such as random or block copolymers. These polymers are used in many areas but do not have the structural and functional complexity of defined sequence biopolymers, such as oligonucleotides, nucleic acids, proteins peptides, or oligosaccharides.

There is great utility in defined monomer sequence polymers, i.e. polymers which are assembled from a library of functional building blocks so that the monomer order is exactly defined, and in which at least two or more of the monomers are structurally distinct from each other. For such molecules it may be possible to programme their structural properties, for example folding and self-assembly, and also their macroscopic properties (Lutz J-F et al., "Sequence-Controlled Polymers", Science 9 Aug. 2013, Vol 341, page 628). Many applications in medicine are also envisaged (Hartmann L and Borner H G, "Precision Polymers: Monodisperse, Monomer-Sequence-Defined Segments to Target Future Demands of Polymers in Medicine" Advanced Materials. 2009, Vol 21, pp 3425-3431).

A key challenge for defined monomer sequence polymers is how to prepare them. Various strategies have been proposed, including biological methods and chemical synthesis using iterative steps in which the monomers are attached one-by-one in a given order. This method suffers from the difficulties of purification at each step. This challenge has been addressed to date (Lutz J-F et al., "Sequence-Controlled Polymers", Science 9 Aug. 2013, Vol 341, page 628; and Hartmann L and Borner H G, "Precision Polymers: Monodisperse, Monomer-Sequence-Defined Segments to Target Future Demands of Polymers in Medicine" Advanced Materials, 2009, Vol 21, pp 3425-3431) through either advanced polymerisation chemistry or solid phase synthesis as used for sequence defined biopolymers, such as oligonucleotides and peptides.

U.S. Pat. No. 8,664,357 reports a process for use in the preparation of oligonucleotides, peptides and peptide nucleic acids which comprises synthesizing a first compound in a step (i) and then in a step (ii) separating the first compound from a second compound which is a reaction by-product of the synthesis of the first compound and/or an excess of a reagent used for synthesis of the first compound, by a process of diafiltration, where the membrane used for the diafiltration process is stable in organic solvents and provides a rejection for the first compound which is greater than the rejection for the second compound.

PCT/GB2015/052287 describes the preparation of non-naturally occurring defined monomer sequence polymers, in which two or more monomers having different backbone and/or side chain moieties are iteratively coupled to one another, with the excess unreacted monomers being separated from the growing polymer by membrane diafiltration processes.

However, the preparation of defined monomer sequence polymers using membrane diafiltration techniques has inherent drawbacks. In order for such processes to be effective, the monomers that are iteratively coupled to the growing polymer must have a molecular weight low enough to allow excess unreacted monomers to be permeated through the membrane, thereby allowing the growing polymer to be isolated and/or purified. Problems arise when it is desirable to couple bulky monomers, the excess quantities of which do not readily permeate through the membrane. Selecting a membrane with a larger molecular weight cut-off (MWCO) can often aggravate the problem, and may lead to quantities of the growing polymer being undesirably lost in the permeate.

The present invention was devised with the foregoing in mind.

SUMMARY OF THE INVENTION

According to a first aspect of the present invention there is provided a process for the preparation of a first compound being a defined monomer sequence polymer, in which at least two of the monomeric units are distinct from each other; the process comprising the steps of:
(i) synthesising a backbone portion of the first compound by performing one or more sequential monomeric coupling reactions in a first organic solvent, at least one of the monomeric units used in the sequential monomeric coupling reactions comprising a reactive side chain precursor group, such that the backbone portion comprises one or more reactive side chain precursor groups located at one or more predetermined positions along its length,
(ii) between each coupling reaction, separating a product of said one or more sequential coupling reactions from at least one second compound, which is a reaction by-product of the synthesis of the product and/or an excess of a reagent used for the synthesis of the product, and
(iii) attaching one or more side chains to the one or more reactive side chain precursor groups located along the length of the backbone portion;
wherein during step (ii) the product of said one or more sequential coupling reactions and at least one second compound are dissolved in a second organic solvent and are separated by a process of diafiltration using a membrane that is stable in the organic solvent and which provides a rejection for the product which is greater than the rejection for the second compound.

According to a further aspect of the present invention, there is provided a defined monomer sequence polymer obtained, directly obtained or obtainable by a process defined herein.

DETAILED DESCRIPTION OF THE INVENTION

Definitions

The term "monomer" or "monomeric unit" is used herein to refer to a polymer building block which has a defined molecular structure and which can be reacted to form a part of a polymer. It will be understood that these terms refer to the minimum repeating unit when any reactive side chain precursor group present is taken into consideration.

The term "defined monomer sequence polymer" is used herein to refer to a polymer comprising at least two monomeric units in which at least two of the monomeric units are distinct from each other and in which the monomeric units are present in the same order in the polymer chain for all molecules of the polymer.

The term "synthesis support" is used herein to relate to a chemical entity that allows the first compound to stay in solution during the reaction and diafiltration step, and optionally to provide an increased molecular bulk to enhance membrane separation. The synthesis support may be a branch point molecule, or a polymer, dendrimer, dendron, hyperbranched polymer, or organic/inorganic materials, including nanoparticles, fullerenes and 2-D materials such as graphene and boron nitride.

The term "branch point molecule" is used herein to refer to a polyfunctional organic molecular "hub", having at least 2 reactive moieties, and the ability to covalently bind to a terminal of an initial monomeric unit.

Processes of the invention

As discussed hereinbefore, the present invention provides a process for the preparation of a first compound being a defined monomer sequence polymer, in which at least two of the monomeric units are distinct from each other; the process comprising the steps of:
  (i) synthesising a backbone portion of the first compound by performing one or more sequential monomeric coupling reactions in a first organic solvent, at least one of the monomeric units used in the sequential monomeric coupling reactions comprising a reactive side chain precursor group, such that the backbone portion comprises one or more reactive side chain precursor groups located at one or more predetermined positions along its length;
  (ii) between each coupling reaction, separating a product of said one or more sequential coupling reactions from at least one second compound, which is a reaction by-product of the synthesis of the product and/or an excess of a reagent used for the synthesis of the product, and
  (iii) attaching one or more side chains to the one or more reactive side chain precursor groups located along the length of the backbone portion;

wherein during step (ii) the product of said one or more sequential coupling reactions and at least one second compound are dissolved in a second organic solvent and are separated by a process of diafiltration using a membrane that is stable in the organic solvent and which provides a rejection for the product which is greater than the rejection for the second compound.

To date, defined monomer sequence polymers prepared by sequential monomeric coupling reactions with intervening membrane diafiltration purification/isolation steps have suffered certain drawbacks. Perhaps most notably is the fact that for such processes to be effective, the monomeric units that are iteratively coupled to the growing polymer must have a molecular weight low enough to allow excess unreacted monomeric units to be permeated through the membrane. This prevents the iterative coupling of monomeric units having bulky side chains—an undesirable limitation. In fact, many of the areas in which defined monomer sequence polymers hold promise rely on the ability to prepare polymers having a predetermined quantity of comparatively larger groups distributed along the length of the polymer at predetermined positions. For example, within the field of medicine, it may be desirable to prepare a polymer that is decorated with a specific therapeutic ratio of active pharmaceutical ingredients (APIs), wherein said ratio can be controlled by the nature of the monomeric units used to prepare the polymer. Alternatively, it may be desirable to prepare a polymer that is decorated with a given ratio of APIs to molecular targeting agents or imaging agents. The present invention facilitates the preparation of such polymers.

The present invention provides a controlled and flexible approach to preparing defined monomer sequence polymers. With the help of intervening membrane diafiltration purification/isolation steps, a backbone portion of the defined monomer sequence polymer can be prepared according to a predetermined sequence of monomeric units. One or more of the monomeric units coupled during the preparation of the backbone may be decorated with a reactive side chain precursor group, which, after completion of the backbone portion, is coupled to a side chain having a complementary reactivity. The finished defined monomer sequence polymer may therefore be endowed with one or more side chains, of any molecular weight, located at predetermined positions along the length of the polymer.

The term "reactive side chain precursor group" refers to any chemical group that is (i) itself able to react with a portion of a desired side chain in such a manner that attaches the side chain to the backbone portion of the defined monomer sequence polymer in which (or on which) the reactive side chain precursor group is located; or (ii) capable of being chemically converted (via one or more steps known to persons of skill in the art) to an alternative chemical group that is able to react with a portion of a desired side chain in such a manner that attaches the side chain to the backbone portion of the defined monomer sequence polymer in which (or on which) the reactive side chain precursor group is located. The reactive side chain precursor group may be a functional group.

It will be understood that the reactive side chain precursor groups may be formed integrally within the backbone portion of the defined monomer sequence polymer (e.g. a —C≡C— group located within the backbone itself). Alternatively, the reactive side chain precursor groups may be pendant to the backbone portion (e.g. a pendant —$CO_2H$ group located on the backbone). It will be further understood that when a reactive side chain precursor group is a pendant group, it may be connected to the backbone by any suitable linker moiety (e.g. an alkylene linker).

In an embodiment, step (i) comprises synthesising a backbone portion comprising a first reactive side chain precursor group and a second reactive side chain precursor group, and step (iii) comprises attaching a first side chain to the first reactive side chain precursor group and a second side chain to the second reactive side chain precursor group.

For illustrative purposes, Scheme 1 below schematically illustrates a backbone portion comprising a first reactive side chain precursor group ($G^1$) and a second reactive side chain precursor group ($G^2$) being derivatised by the addition of a first side chain ($SC^1$) and a second side chain ($SC^2$).

Scheme 1

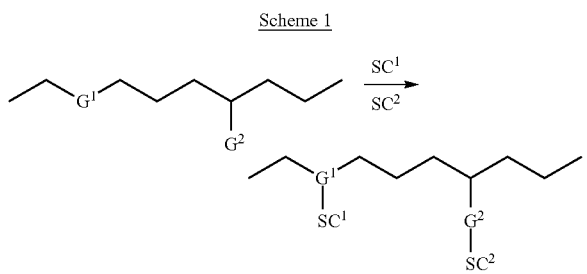

Scheme 2

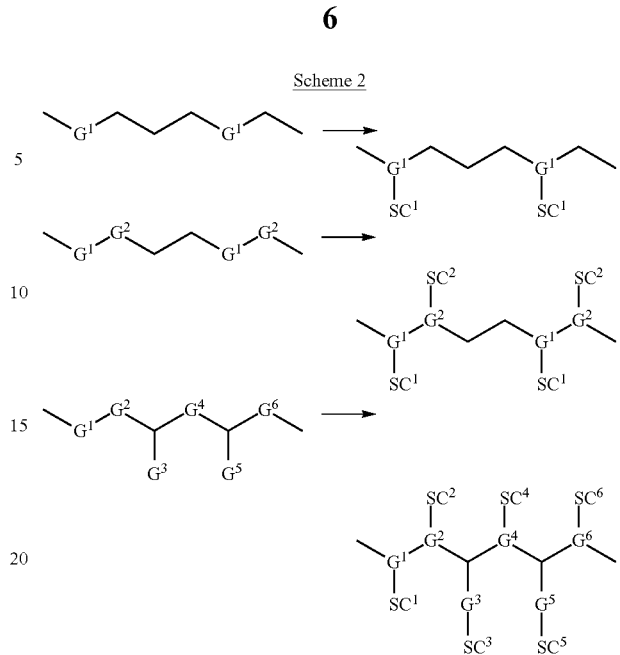

In an embodiment, the first and second reactive side chain precursor groups are identical. Alternatively, the first and second reactive side chain precursor groups are different.

In another embodiment, the first and second side chains are the same. Alternatively, the first and second side chains are different.

When step (i) comprises synthesising a backbone portion comprising a first reactive side chain precursor group and a second reactive side chain precursor group, it will be understood that the first and second reactive side chain precursor groups may be located on the same monomeric unit used in the one or more sequential coupling reactions, or the first and second reactive side chain precursor groups may be located on separate monomeric units used in the coupling reactions. Suitably, a first monomeric unit used in the one or more sequential monomeric coupling reactions comprises the first reactive side chain precursor group and a second monomeric unit used in the one or more sequential monomeric coupling reactions comprises the second reactive side chain precursor group.

In an embodiment, the first reactive side chain precursor group is configured to react exclusively with the first side chain, and the second reactive side chain precursor group is configured to react exclusively with the second side chain. In such embodiments, the first and second side chains may be reacted with the backbone portion in a single step. Alternatively, the first and second side chains may be separately reacted with the backbone.

In another embodiment, step (i) comprises synthesising a backbone portion comprising a number of reactive side chain precursor groups, $n_1$, and step (iii) comprises attaching a number of side chains, $n_2$, to the reactive side chain precursor groups, wherein $n_1$ and $n_2$ are each independently an integer between 1 and 100. $n_1$ and $n_2$ can be the same or different, although it will be appreciated that the number of side chains ($n_2$) cannot exceed the number of reactive side chain precursor groups ($n_1$). Suitably $n_1$ and $n_2$ are each independently an integer between 2 and 75. More suitably, $n_1$ and $n_2$ are each independently an integer between 3 and 50. It will be appreciated that where $n_1$ is greater than 1, the reactive side chain precursor groups may be the same or different. Similarly, it will be appreciated that where $n_2$ is greater than 1, the side chains may be the same of different.

For illustrative purposes, Scheme 2 below schematically illustrates shows a variety of backbones prepared in accordance with step (i) being derivatised with a variety of side chains in accordance with step (iii).

In an embodiment, the one or more reactive side chain precursor groups each comprise a functional group. It will be understood that the nature of the side chain intended to be attached to the backbone at that position will influence the type of functional group selected. Any suitable functional group may be selected, provided it has a reactivity that is complementary to the side chain that is intended to be coupled at that position. Suitably, the functional group is selected from —OH, —$NH_2$, —C≡C—, —SH, —$CO_2$H, —$ONH_2$, —CHO, —$B(OH)_2$, —CH(OH)CH2OH (1,2-diols), —CH(O)$CH_2$ (epoxide), —CH(NR)$CH_2$ (aziridine), —CH($OSO_3$)$CH_2$ (cyclic sulfate), —$PR_2$ (phosphines), —$N_3$ and —CH=$CH_2$.

In another embodiment, the functional group is selected from an epoxide, an aziridine, a cyclic sulphate and a phosphine.

In another embodiment, the functional group is selected from —$OR_1$, —$NR_1R_2$, —C≡$CR_1$, —$SR_1$, —$CO_2R_1$, —$CH_2OCH_2CO_2R_1$, —$ONR_1R_2$, —CHO, —$B(OH)_2$, —CH(OH)$CH_2$OH (1,2-diols), —CH(O)$CH_2$, —CH(NR)$CH_2$, —CH($OSO_3$)$CH_2$, —$PR_1R_2$, —$N_3$, and —CH=$CR_1R_2$,
  wherein $R_1$ and $R_2$ are each independently selected from hydrogen, (1-4C)alkyl, aryl, heteroaryl, aryl(1-2C)alkyl and heteroaryl(1-2C)alkyl, any of which may be optionally substituted with one or more substituents selected from halo, (1-4C)alkyl and (1-4C)alkoxy.

Suitably, the functional group is selected from —$NH_2$, —C≡CH, —$OR_1$, —$SR_1$ and —$N_3$,
  wherein $R_1$ is selected from hydrogen, (1-4C)alkyl, aryl, heteroaryl, aryl(1-2C)alkyl and heteroaryl(1-2C)alkyl, any of which may be optionally substituted with one or more substituents selected from halo, (1-4C)alkyl and (1-4C)alkoxy.

More suitably, the functional group is selected from —$NH_2$, —C≡CH, benzyl ether-(—OBn), 4-methoxybenzyl thioether-(—SPmb) and —$N_3$.

In another embodiment, each side chain independently comprises a group selected from targeting molecules (e.g. a specific ligand or antibody), active pharmaceutical ingredients, imaging agents, sugars, amino acids, peptides, nucleobases, aptamers, oligonucleotides, and monodisperse synthetic polymers.

The monodisperse synthetic polymer may be, for example, a poly(alkylene glycol). When a series of monodisperse synthetic polymers are coupled to the backbone in accordance with the present invention, the resultant defined monomer sequence polymer may resemble a brush polymer (also known as graft or comb polymer).

Alternatively, the target molecules with which the defined monomer sequence polymer reacts include portions of biological molecules such as proteins, sugars, glycoproteins and lipids.

In an embodiment, the side chain has been modified such that a portion of it (e.g. a terminus) contains a functional group that is complementary to the reactive side chain precursor group located on the backbone. The side chain may have been modified with any one of those functional groups recited herein in respect of the side chain precursor group.

In another embodiment, the side chain may be attached to the backbone portion via a labile group. Suitably, the labile group allows the side chain(s) (or a portion thereof) to be detached from the backbone portion in response to a change in conditions (for example temperature, pH, the expression of certain enzymes or one or more conditions being specific to a disease site microenvironment). Such embodiments therefore allow the preparation of defined monomer sequence polymers that are able to release a biologically active payload (e.g. an API) at a desired site within an organism. In such embodiments, the present invention permits the preparation of defined monomer sequence polymers having a molecular weight suitable for achieving effective delivery of an active ingredient within an organism. For example, the present invention permits the preparation of defined monomer sequence polymers having a molecular weight greater than the glomerular filtration threshold required for renal clearance, meaning that the defined monomer sequence polymer is circulated in the organism for a prolonged period of time. Alternatively, the defined monomer sequence polymers may be prepared to have a molecular weight that is lower than the glomerular filtration threshold required for renal clearance, meaning that the polymer is readily cleared from the body after having released its payload.

The labile group may be part of the reactive side chain precursor group, or part of the side chain.

In an embodiment, step (iii) comprises reacting an excess of the one or more side chains with the product of step (ii), and then separating the unreacted side chains from the reaction product (i.e. the side chain-containing monomer-sequence-defined polymer) by a process of diafiltration using a membrane which provides a rejection for the reaction product that is remarkably greater than the rejection for the unreacted side chain. Suitably, the separation step is conducted in an organic solvent.

In another embodiment, all of the monomeric units used in the one or more sequential monomeric coupling reactions of step (i) have identical backbone moieties. It will be understood that the term "backbone moiety" in reference to the monomeric units does not include any reactive side chain precursor groups that may be present. Hence, all of the monomeric units used in the one or more sequential monomeric coupling reactions of step (i) may have an ethylene glycol backbone but they may each have different reactive side chain precursor groups pendant to the ethylene glycol backbone.

Suitably, the backbone portion of the first compound is homopolymeric and is selected from poly(alkylene glycol), polysiloxanes (e.g. poly(dimethylsiloxane) (PDMS)), polybutadiene, polysioprene, polystyrene, nylons and polyesters, poly(ethylene imines) (PEI), poly(propylene imines), poly(L-lysine) (PLL), poly(amidoamines) (PAA), poly(methyl methacrylate) (PMMA), poly(vinyl benzoic acid), poly(hydroxystyrene), N-substituted glycines, and poly(lactide-co-glycolide) (PLGA). Although the backbone portion is homopolymeric, a plurality of different reactive side chain precursor groups may be located along its length. More suitably, the backbone portion of the first compound is a homopolymeric poly(alkylene glycol). Most suitably, the backbone portion of the first compound is a poly(ethylene glycol).

In a particular embodiment, the backbone portion of the first compound is a poly(alkylene glycol) (e.g. a poly(ethylene glycol). For such embodiments, the monomeric units that are coupled during the one or more sequential monomeric coupling reactions may each independently comprise a 1-mer alkylene glycol backbone moiety, or a 3-7-mer poly(alkylene glycol) backbone moiety. Irrespective of the number of alkylene glycol repeat units, it will be understood that the term "monomeric unit" refers to a minimum repeating unit including any reactive side chain precursor group that is present. Exemplary monomeric units useful in step (i) are tetragol-based units (tetraethylene glycol-based). An example of a tetragol-based monomeric unit useful in step (i) is shown below:

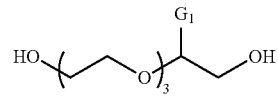

where $G_1$ is a reactive side chain precursor group. It will be understood that hydroxyl-protected forms may be more suitable for used as part of the present invention. Pentagol-based (pentaethylene glycol-based) monomeric units may also be used.

In another embodiment, the monomeric units used in the one or more sequential monomeric coupling reactions of step (i) have siloxane-containing backbone moieties. In such embodiments, the backbone portion of the first compound may be a poly(siloxane).

In an alternative embodiment, not all of the monomeric units used in the one or more sequential monomeric coupling reactions of step (i) have identical backbone moieties.

Suitably, the backbone portion of the first compound is a copolymer formed from two or more of ethylene glycol, propylene glycol, butylene glycol, siloxanes (e.g. dimethylsiloxane), butadiene, isoprene, styrene, amides and esters, ethylene imines, propylene imines, L-lysine, amidoamines, methyl methacrylate, vinyl benzoic acid, hydroxystyrene, N-substituted glycines, lactide-co-glycolide.

Having regard to step (i), it will be understood that the "first compound" may be a defined monomer sequence polymer containing only two monomeric units, in which case the polymer is synthesised by the coupling of an initial monomeric unit with a first additional monomeric unit. It will also be understood that the "first compound" may be a defined monomer sequence polymer containing three monomeric units, in which case the polymer is synthesised by first coupling an initial monomeric unit with a first additional monomeric unit, then coupling the first additional monomeric unit with a second additional monomeric unit. Accordingly, "first compounds" containing 4, 5 and 6 monomeric units are respectively synthesised by sequential coupling of the third, fourth and fifth additional monomeric units to the second, third and fourth additional monomeric units respectively.

Still having regard to step (i), any suitable method of synthesising the first compound that is known in the art may be utilised. In an embodiment, the synthesis of the first compound may involve one or more coupling and deprotection reactions. In such cases, step (i) comprises reacting an initial monomeric unit with an excess of a first additional monomeric unit in which one of the reactive terminals has been protected using a protecting group. Once the initial monomeric unit and the first additional monomeric unit have been coupled, the protecting group is cleaved to expose the reactive terminal of the first additional monomeric unit, which is then ready for coupling with a second additional monomeric unit. Hence, in an embodiment, the one or more monomeric coupling reactions of step (i) each comprise the steps of:

a. reacting a starting material with an excess of an additional monomeric unit, the additional monomeric unit having one or its reactive terminal protected by a protecting group, and
b. removing the protecting group so as to expose the reactive terminal such that it is ready for reaction with a subsequent additional monomeric unit, wherein the starting material is either an initial monomeric unit having at least one of its reactive terminals protected, or the polymeric product of the one or more sequential monomeric coupling reactions. In such embodiments, step (ii) may be performed after step a) (in order to remove excess unreacted additional monomers and optionally other small reaction debris) and after step b) (in order to remove the cleaved protecting group, by-products of the protecting group removal and one or more deprotection reagents). It will be understood that the term "reagent" appearing in step (ii) encompasses both reactants and catalysts.

In one embodiment, during synthesis of the first compound, the product of the one or more sequential monomeric coupling reactions is covalently attached to a synthesis support by an initial monomeric unit. The initial monomeric unit may be directly attached to the synthesis support, or indirectly attached thereto via a linker moiety (such as a dicarboxylic acid moiety). The synthesis support may be a branch point molecule, or a polymer, dendrimer, dendron, hyperbranched polymer, or organic/inorganic nanoparticle. Once the backbone portion of the desired defined monomer sequence polymer has been synthesised, the synthesis support is cleaved from the initial monomeric unit and separated therefrom.

When used as a synthesis support, suitable polymers include polycondensation matrices or polymerisation matrices containing heteroatom functions. Such heteroatom functions may contain oxygen, nitrogen, or can contain more than one heteroatom, such as acid amide groups. Examples of polymeric synthesis supports include polyalkylene glycols including polyethylene glycol, polycaprolactone, polyethylene glycol esterified with citric acid, copolymers of polyethyleneglycol and succinic acid, of vinylpyrrolidone and acrylic acid or beta-hydroxy-ethylacrylate, or of acrylamide and vinylactetate.

When used as a synthesis support, suitable dendrimers include poly(amidoamine), also known as PAMAM dendrimers; phosphorous dendrimers; polylysine dendrimers; and polypropylenimine (PPI) dendrimers which can have surface functionalities including —OH, —NH$_2$, —PEG, and COOH groups.

When used as a synthesis support, suitable nanoparticles may be prepared from SiO$_2$, TiO$_2$, or other organic or inorganic materials including fullerenes or 2-D materials such as graphene.

In another embodiment, the synthesis support is a branch point molecule (i.e. a polyfunctional molecule) having two or more reactive moieties capable of covalently binding to the initial monomeric unit. Chemistries suitable for covalently binding the initial monomeric unit to the branch point molecule will be readily apparent to a person of skill in the art, and include amide, ester, ether and silyl ether couplings.

In another embodiment, the branch point molecule may have any of the structures shown below:

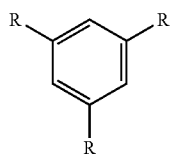

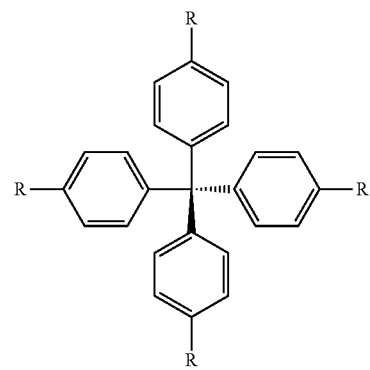

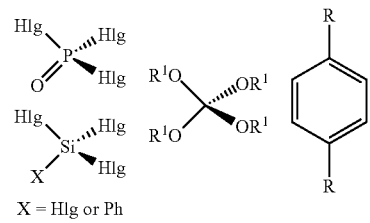

X = Hlg or Ph

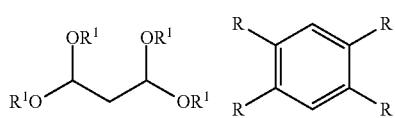

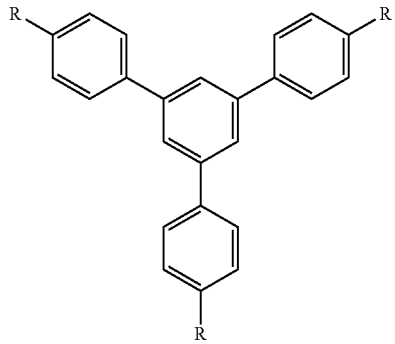

-continued

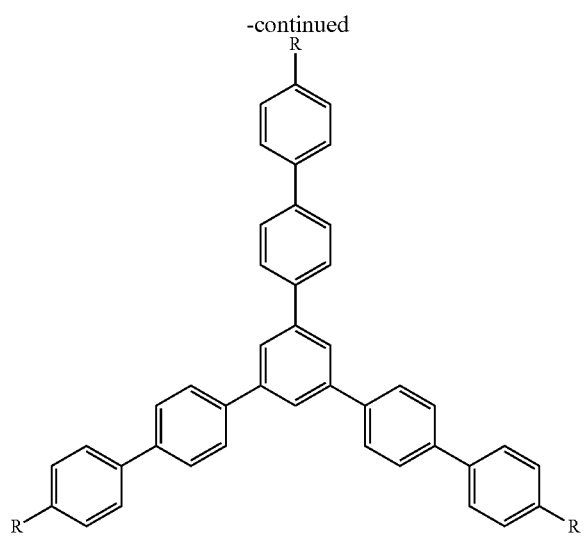

Hlg = Halogen
R = COOH, COHlg, CH$_2$Hlg
R$^1$ = alkyl

In an embodiment, the initial monomeric unit is reacted in excess with a synthesis support, allowing for the synthesis of a conjugate that can be purified from the excess initial monomeric unit. Subsequently, the first compound may be obtained through a succession of coupling/deprotection reactions using one or more additional monomeric units.

The choice of the cleavage reaction used to detach the backbone portion from the branch point molecule is dependent on the product one desires to synthesise and can be performed at the end of the synthetic strategy or at any stage, according to convenience.

In another embodiment, the first solvent (i.e. that used in step (i)) and the second solvent (i.e. that used in step (ii)) may be the same or different. Suitably, the solvent used for the diafiltration should maintain the polymer and/or the functionalised polymer in solution. Exemplary solvents include aromatics, alkanes, ketones, glycols, chlorinated solvents, esters, ethers, amines, nitriles, aldehydes, phenols, amides, carboxylic acids, alcohols, furans, and dipolar aprotic solvents, and mixtures thereof and with water. Specific examples of solvents include toluene, xylene, benzene, styrene, anisole, chlorobenzene, dichlorobenzene, chloroform, dichloromethane, dichloroethane, methyl acetate, ethyl acetate, butyl acetate, methyl ether ketone (MEK), methyl isobutyl ketone (MIBK), acetone, ethylene glycols, ethanol, methanol, propanol, butanol, hexane, cyclohexane, dimethoxyethane, methyl tert-butyl ether (MTBE), diethyl ether, adiponitrile, N,N-dimethylformamide, dimethylsulfoxide, N,N-dimethylacetamide, dioxane, nitromethane, nitrobenzene, pyridine, carbon disulfide, tetrahydrofuran, methyl-tetrahydrofuran, N-methyl pyrrolidone, N-ethyl pyrrolidone, acetonitrile, and mixtures thereof and with water.

Suitable membranes for use in the invention include polymeric and ceramic membranes, and mixed polymeric/inorganic membranes. Membrane rejection $R_i$ is a common term known by those skilled in the art and is defined as:

$$R_i = \left(1 - \frac{C_{P_i}}{C_{R_i}}\right) \times 100\% \qquad \text{eq. (1)}$$

where $C_{P,i}$=concentration of species i in the permeate, permeate being the liquid which has passed through the membrane, and $C_{R,i}$=concentration of species i in the retentate, retentate being the liquid which has not passed through the membrane. It will be appreciated that a membrane is suitable for the invention if R(defined monomer sequence polymer OR conjugate)>R(at least one reaction by-product or reagent).

Membrane processes are well known in the art of separation science, and can be applied to a range of separations of species of varying molecular weights in liquid and gas phases (see for example "Membrane Technology" in Kirk Othmer Encyclopedia of Chemical Technology, 4$^{th}$ Edition 1993, Vol 16, pages 135-193). Nanofiltration is a membrane process utilising membranes whose pores are in the range 0.5-5 nm, and which have MW cutoffs of 200-3,000 Daltons. Nanofiltration has been widely applied to filtration of aqueous fluids, but due to a lack of suitable solvent stable membranes has not been widely applied to separation of solutes in organic solvents. Ultrafiltration membranes typically have MW cutoffs in the range 3,000 to 1,000,000 Daltons. Recently new classes of membranes have been developed which are stable in even the most difficult solvents as reported in P. Marchetti, M. F. Jimenez-Solomon, G. Szekely, A. G. Llvingston Chem. Rev., (2014), Vol 114, pages 10735-10806. These may be polymeric membranes or ceramic membranes, or mixed inorganic/organic membranes. Some of these membranes are suitable for Organic Solvent Nanofiltration (OSN).

The membranes useful as part of the present invention may be formed from any polymeric or ceramic material which provides a separating layer capable of preferentially separating the first molecule or conjugate from at least one reaction by-product or reagent. Preferably the membrane is formed from or comprises a material selected from polymeric materials suitable for fabricating microfiltration, ultrafiltration, nanofiltration or reverse osmosis membranes, including polyethylene, polypropylene, polytetrafluoroethylene (PTFE), polyvinylidene difluoride (PVDF), polysulfone, polyethersulfone, polyacrylonitrile, polyamide, polyester, polyimide, polyetherimide, cellulose acetate, polyaniline, polypyrrole, polybenzimidazole, polyetheretherketone (PEEK) and mixtures thereof. The membranes can be made by any technique known in the art, including sintering, stretching, track etching, template leaching, interfacial polymerisation or phase inversion. More preferably, membranes may be cross-linked or treated so as to improve their stability in the reaction solvents. PCT/GB2007/050218, PCT/GB2011/051361 and PCT/GB2015/050179 describe membranes which may be suitable for use in the present invention.

In a particular embodiment, the membrane is a composite material and the non-porous, selectively permeable layer thereof is formed from or comprises a material selected from modified polysiloxane based elastomers including polydimethylsiloxane (PDMS) based elastomers, ethylene-propylene diene (EPDM) based elastomers, polynorbornene based elastomers, polyoctenamer based elastomers, polyurethane based elastomers, butadiene and nitrile butadiene rubber based elastomers, natural rubber, butyl rubber based elastomers, polychloroprene (Neoprene) based elastomers, epichlorohydrin elastomers, polyacrylate elastomers, polyethylene, polypropylene, polytetrafluoroethylene (PTFE), polyvinylidene difluoride (PVDF) based elastomers, polyetherblock amides (PEBAX), polyurethane elastomers, cross-linked polyether, polyamides, polyesters, polyketones, formed by interfacial polymerisation, and mixtures thereof.

In another embodiment, the membrane is prepared from an inorganic material (e.g. silicon carbide, silicon oxide, zirconium oxide, titanium oxide, or zeolites), using any technique known to those skilled in the art such as sintering, leaching or sol-gel processes.

In another embodiment, the membrane comprises a polymer membrane with dispersed organic or inorganic matrices in the form of powdered solids present at amounts up to 20wt % of the polymer membrane. Carbon molecular sieve matrices can be prepared by pyrolysis of any suitable material as described in U.S. Pat. No. 6,585,802. Zeolites as described in U.S. Pat. No. 6,755,900 may also be used as an inorganic matrix. Metal oxides, such as titanium dioxide, zinc oxide and silicon dioxide may be used, for example the materials available from Evonik Industries (Germany) under their Aerosol and AdNano trademarks. Mixed metal oxides such as mixtures of cerium, zirconium, and magnesium oxides may be used. Graphene, graphene oxide, metal organic frameworks (MOFs), boron nitride, carbon nanotubes may be used. Preferred matrices will be particles less than 1.0 micron in diameter, preferably less than 0.1 microns in diameter, and preferably less than 0.01 microns in diameter.

EXAMPLES

Examples of the invention will now be described, for the purpose of illustration only, with reference to the accompanying drawings in which.

Abbreviations

The following abbreviations are used throughout the figures and Examples:
Bn=benzyl;
Dmtr=4,4'-dimethoxytrityl;
Tbdms=tert-butyldimethylsilyl;
Ms=Methanesulfonic;
DMF=dimethyl formamide;
THF=tetrahydrofuran;
DCA=dichloroacetic acid;
NMI=1-methylimidazole;
Tbdps=tert-butyldiphenylsilyl;
TEA=triethylamine
DCM=dichloromethane;
DHP=dihydropyran
BB=building block
HMTETA=1,1,4,7,10,10-hexamethyltriethylenetetramine
TBAF=tetra-n-butylammonium fluoride;
OSN=organic solvent nanofiltration;
PMDETA=N,N,N',N'',N''-pentamethyldiethylenetriamine;
EDC=1-ethyl-3-(3-dimethylaminopropyl)carbodiimide;
NHS=N-hydroxysuccinimide;
PBI=polybenzimidazole;
PEEK=poly(ether ether ketone)

Example 1

Figure 1:
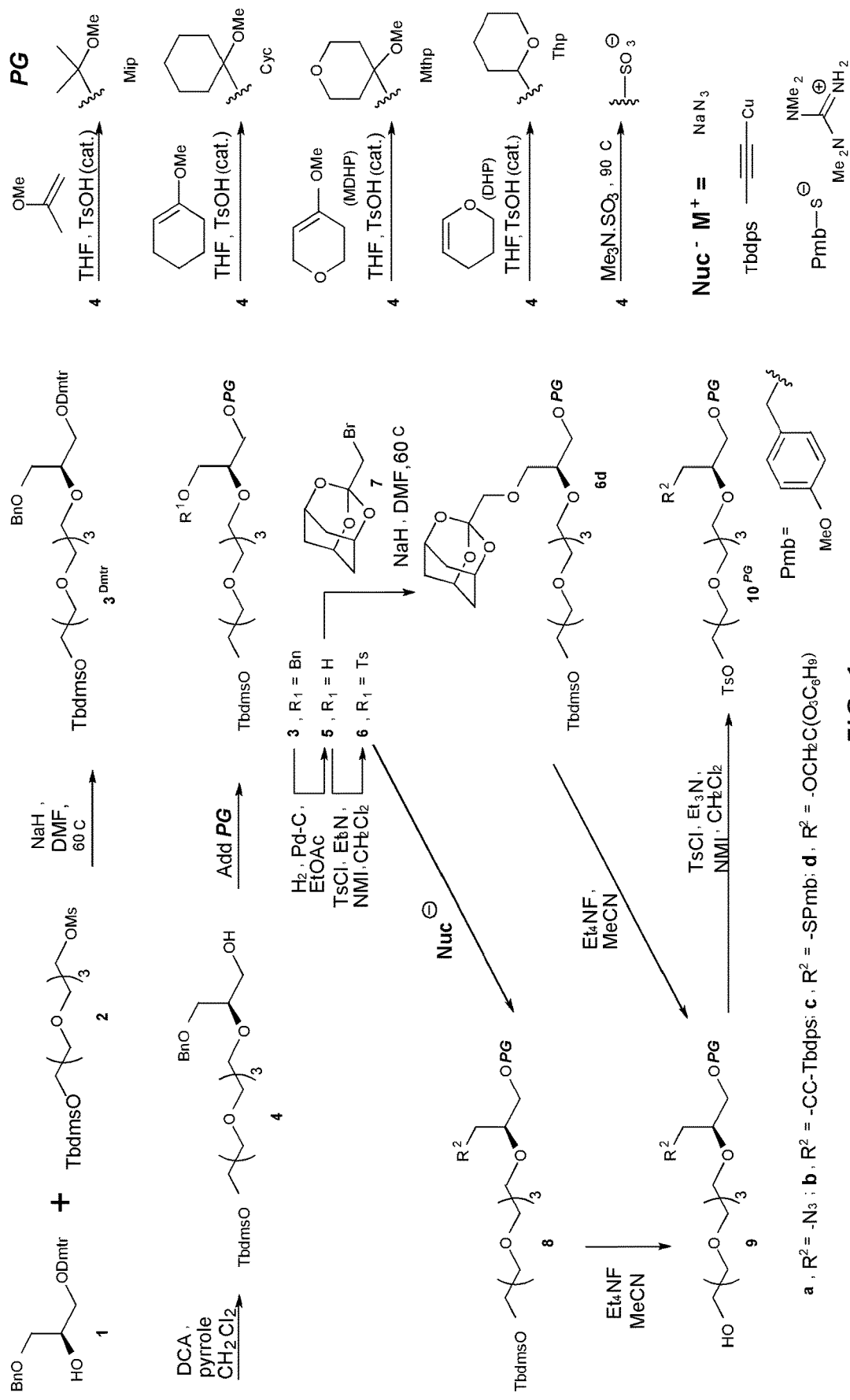
FIG. 1 shows the synthesis routes for various pentagol-based monomer building blocks used for fabrication of PEG defined monomer sequence backbone portions with distinct reactive side chain precursor groups.

FIG. 1 shows four pentagol-containing ($Eg_5$) protected monomeric building blocks (tetragol=(ethylene glycol)$_4$)

with different reactive side chain precursor groups ($R^2$). The monomeric building blocks (BBs) have the general structure TsOEg4OCH(CH$_2$R$^2$)CH$_2$OPG [R$^2$=—N$_3$ (10a), —CC-Tbdps (10b), —SPmb (10c) and —OCH$_2$C(O$_3$C$_6$H$_9$) (10d)], which are obtained according to the synthetic route described in FIG. 1. Different protecting groups [PG=-Dmtr, -Mip, -Cyc, -Mthp, -Thp and —SO$_3^-$] are used for simple protection and effective deprotection, with a range of stability/controllable rate of acid-labile deprotection during each chain-extension cycle.

Figure 2:
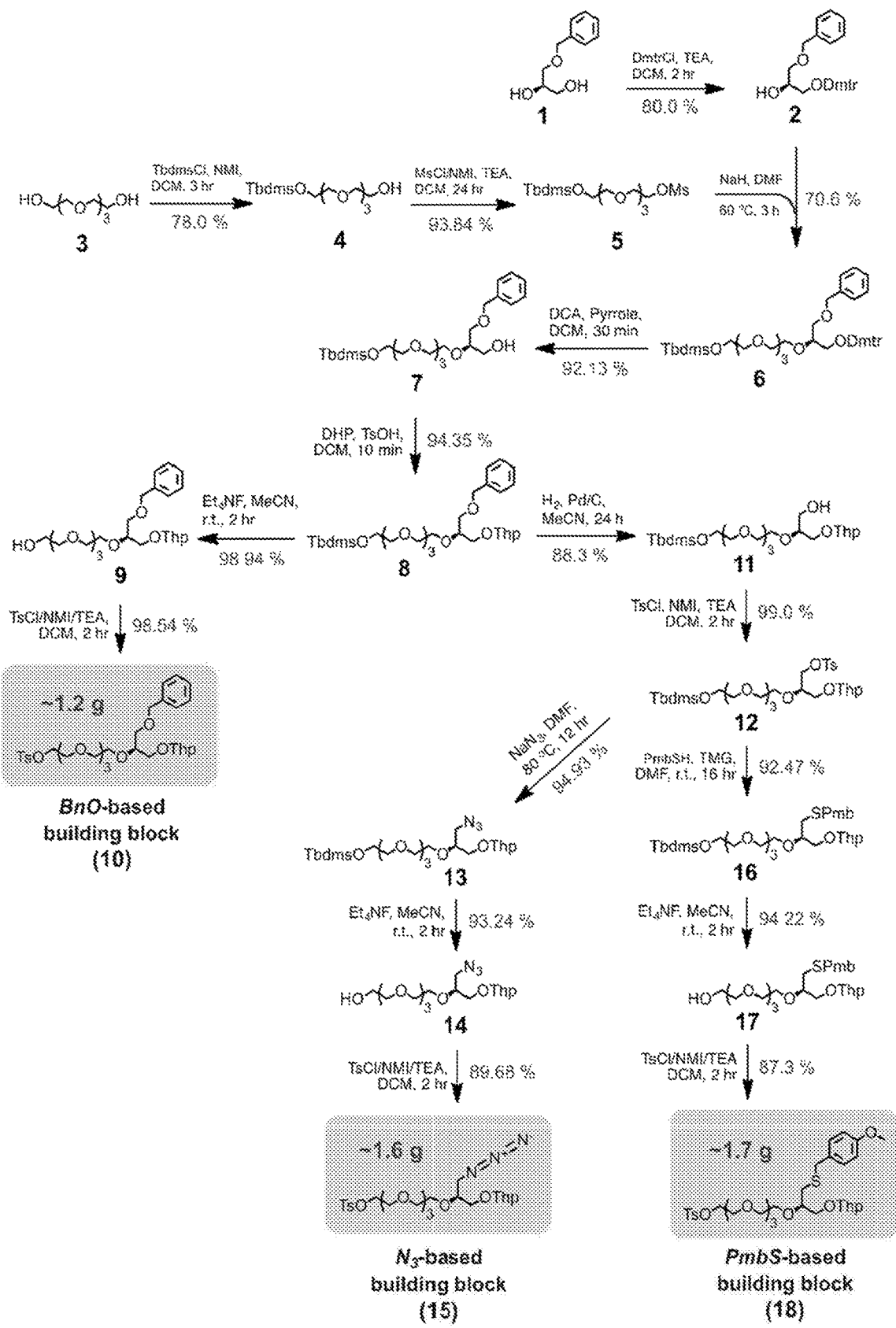
FIG. 2 shows the full synthesis routes for the pentagol-based building blocks BnO—BB, $N_3$—BB and PmbS—BB.

Three hetero-functionalized tetragol derivatives with different reactive side-groups, namely TsO-EG$_4$(R)—OThp (R=—OBn, —N$_3$ and —SPmb), were synthesised as building blocks according to the procedure shown in FIG. 2. Notably, the coupling reaction between compound 2 and compound 5 generates some side products. Thus, it is preferable to completely dry the starting materials using acetonitrile before adding NaH catalyst to initiate the reaction. The hydrogenolysis of compound 8 to produce compound 11 was found to work best in acetonitrile and ethyl acetate. Here, the acid-labile Thp group was selected as a protecting group due to its acid-sensitivity and its small size, which means that it can be both effectively deprotected after each chain-extension cycle and, also easily removed by OSN diafiltration. The Tosyl group has high reactivity with OH group using NaH as a catalyst, making it suitable for chain extension of PEGs. The three different side-groups including BnO—, N$_3$— and PmbS— on these building blocks can be readily converted into highly reactive groups after deprotection procedure, such as —OH, —NH$_2$ and —SH, respectively.

Figure 3:
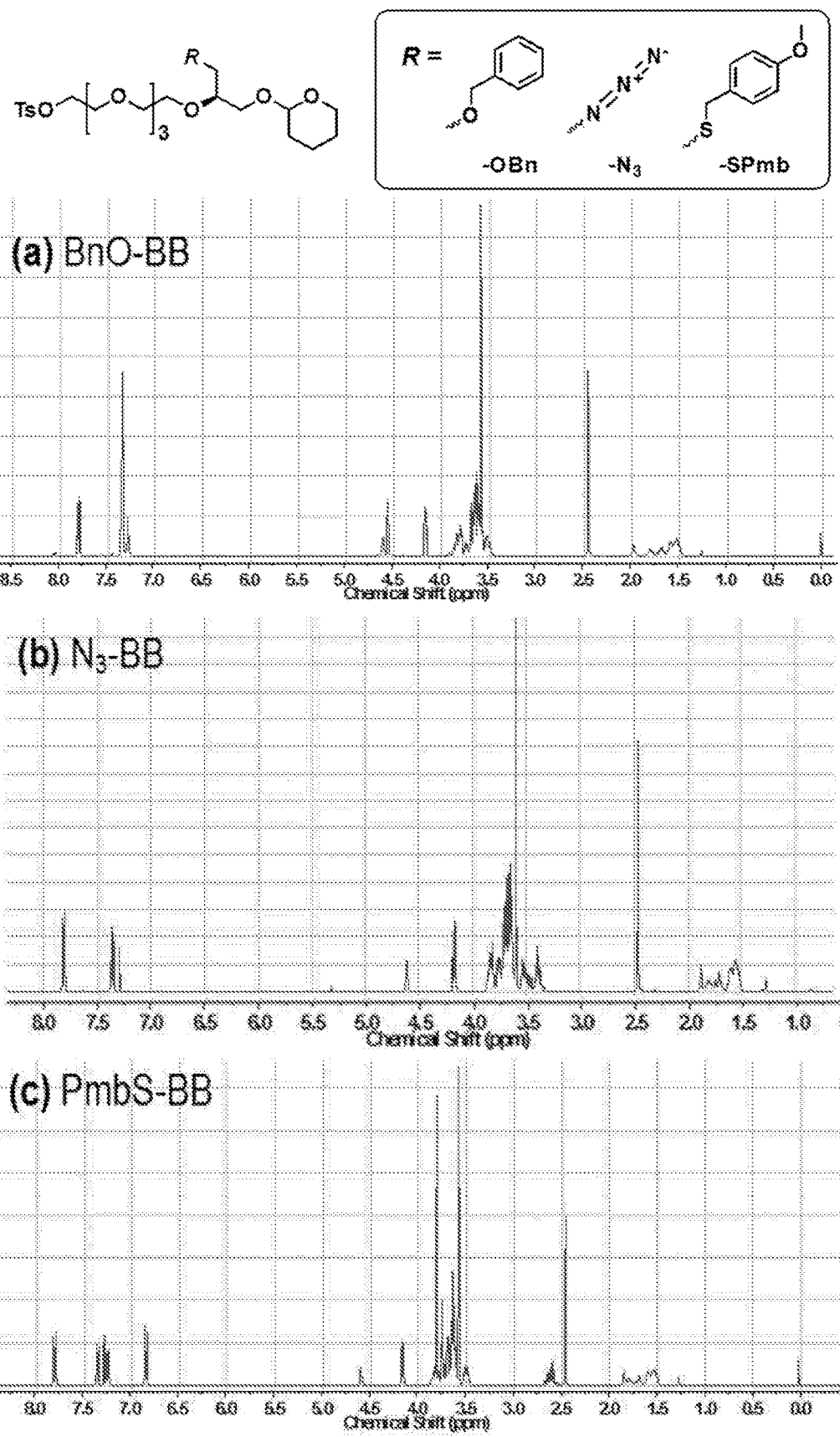
FIG. 3 shows $^1H$ NMR spectra for the building blocks identified in FIG. 2.
Figure 4:
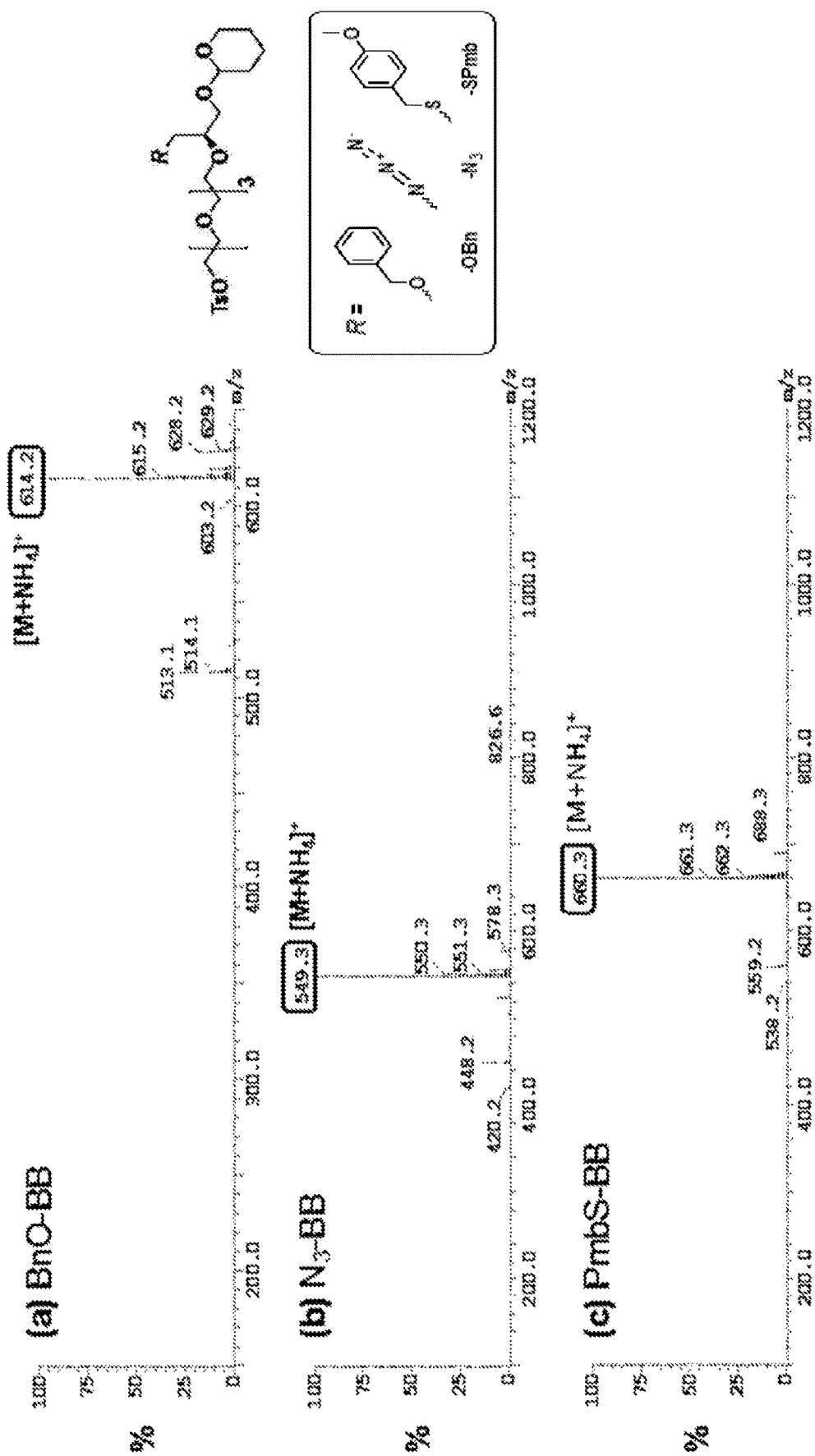
FIG. 4 shows mass spectra for the building blocks identified in FIG. 2.

The chemical structure and molecular weight of the resulting building blocks including BnO—BB, N$_3$—BB and PmbS—BB, have been confirmed by NMR spectroscopy and mass spectroscopy in FIGS. 3 and 4. The clearly observed m/z peaks at 614.2, 549.3 and 660.3 are assigned to BnO—BB, N$_3$—BB and PmbS—BB, respectively.

Example 2

Figure 5:
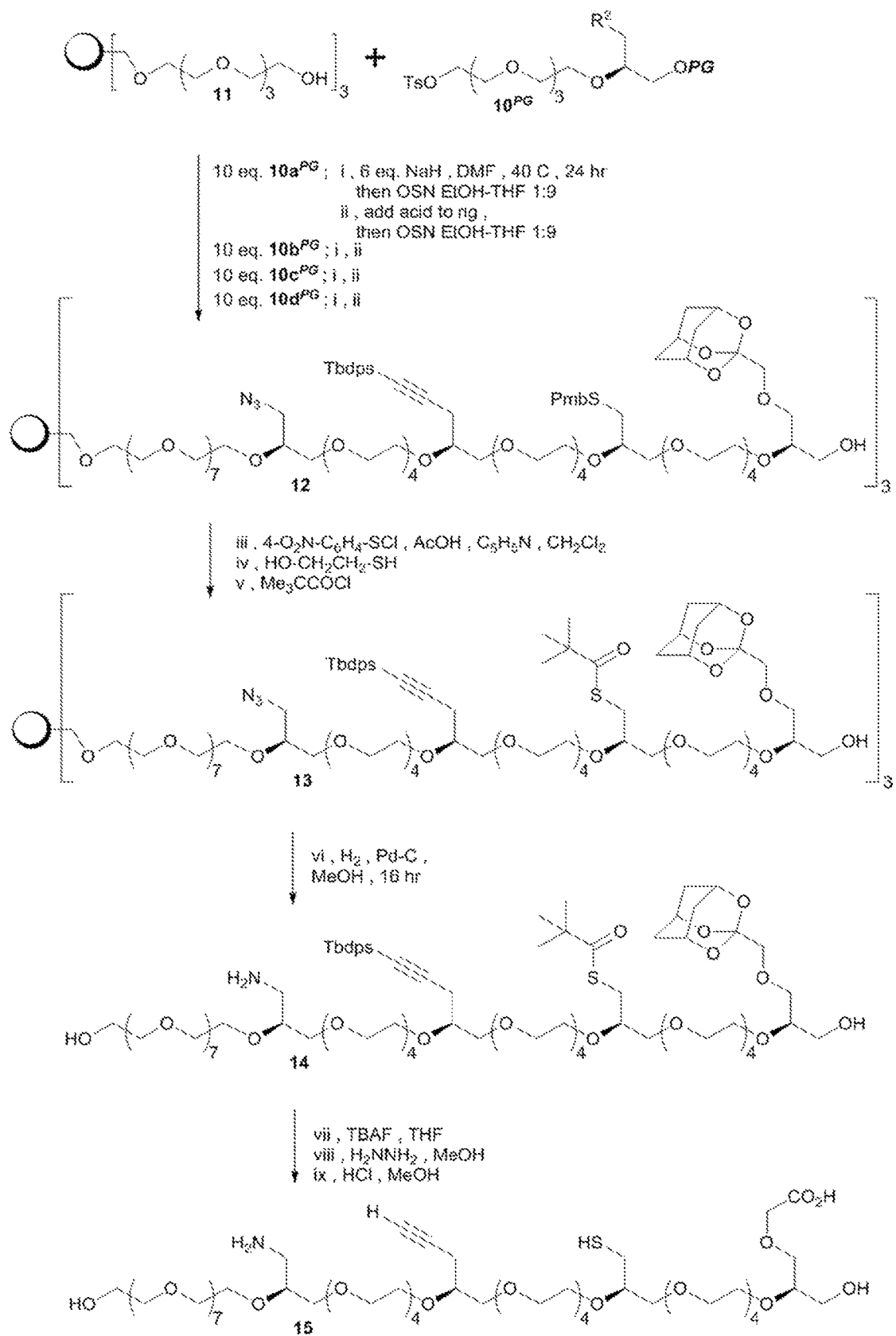
FIG. 5 shows the preparation of sequence-defined PEGs for use as backbone portion with multiple (≥4) reactive side chain precursor groups attached to a synthesis support, and subsequent cleavage from the synthesis support.
Figure 7:
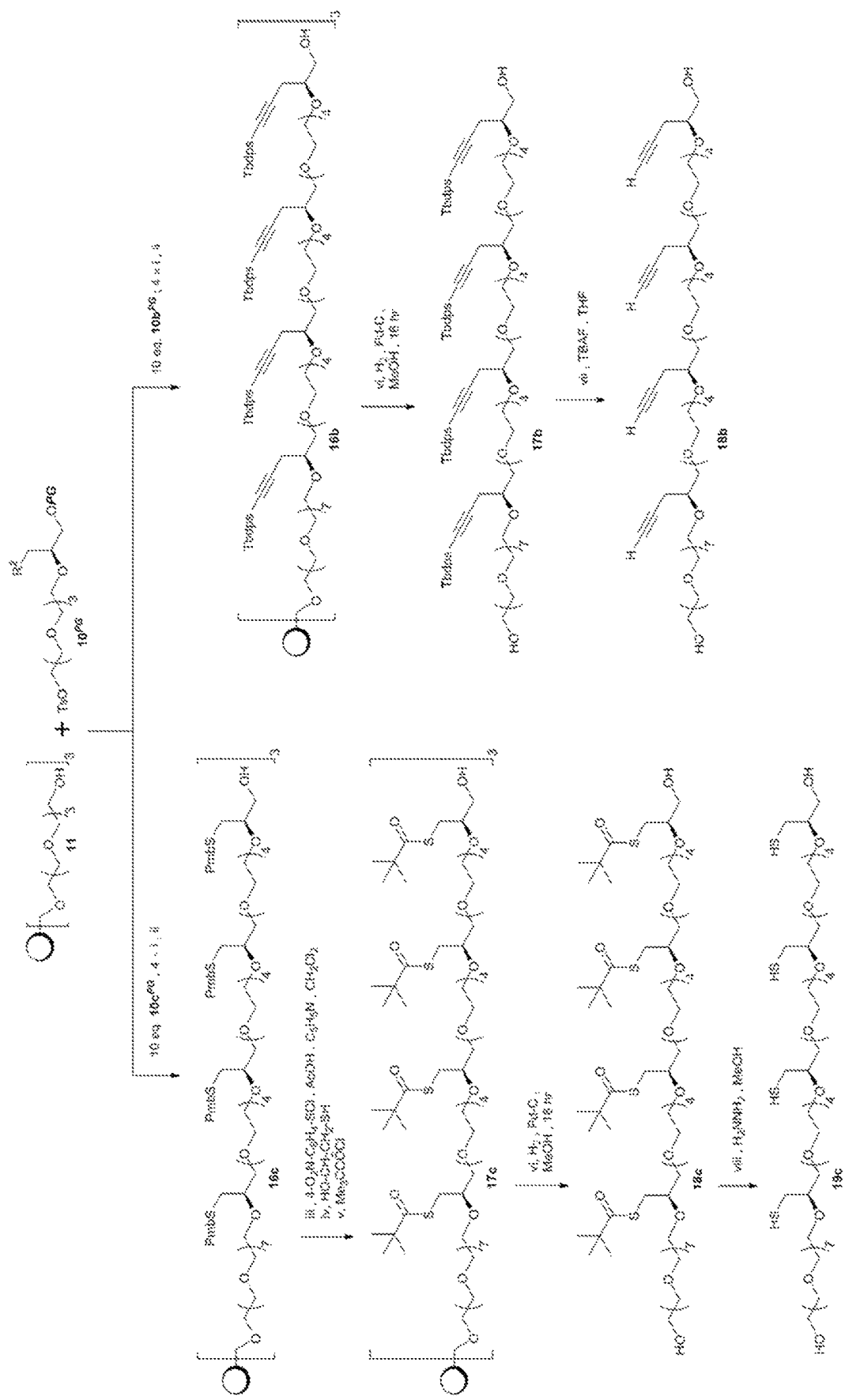
FIG. 7 shows the preparation of sequence-defined PEG backbone portions with identical reactive side chain precursor groups suitable for "click chemistry". Synthesis of the backbone portions on a synthesis support is followed by cleavage from the support.
Figure 9:
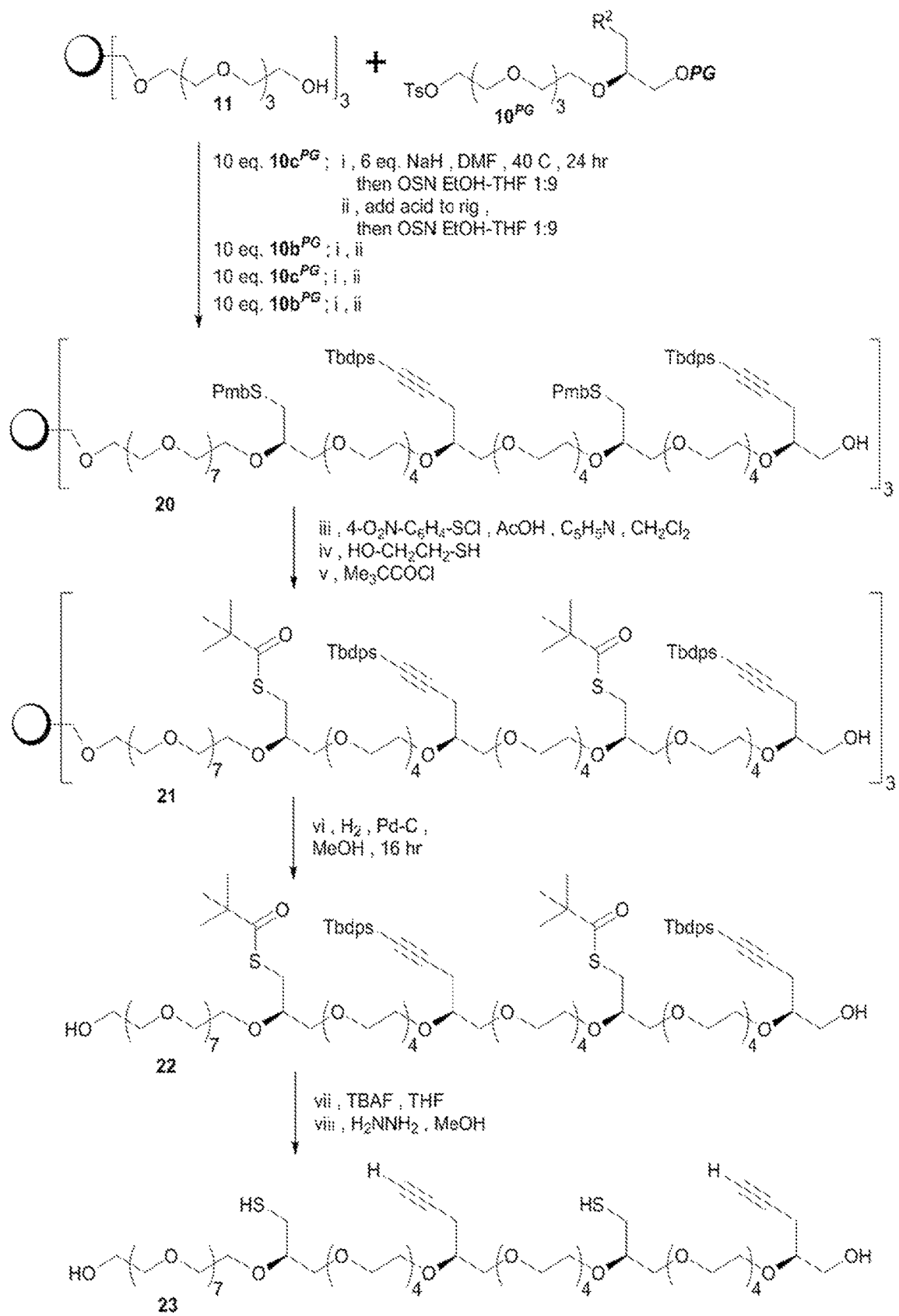
FIG. 9 shows the preparation of a sequence-defined PEG backbone portion containing multiple distinct reactive side chain precursor groups for click chemistry. Synthesis of the backbone portion on a synthesis support is followed by cleavage from the support.

FIGS. 5, 7, and 9 show coupling and deprotection processes used to form suitable defined monomer sequence backbone portions. The monomeric building blocks obtained in FIG. 1 are coupled onto a synthesis support (support-OEg$_4$—OH) in any preselected order, using organic solvent nanofiltration (OSN) technology for purification during each round, to produce monodisperse sequence-defined PEG backbone portions, each bearing up to four possible reactive side chain precursor groups (15 in FIG. 5). PEG backbone portions with identical reactive side chain precursor groups (18b and 19c in FIG. 7), and PEG backbone portions with different reactive side chain precursor groups (23 in FIG. 9) are also prepared. These defined monomer sequence backbone portion PEGs have a plurality of identical or different reactive side chain precursor groups, which can then be post-conjugated with a large range of side chains. In addition, the "clickable" reactive side chain precursor groups (e.g. —SH and —C≡CH) incorporated into these monodisperse sequence-defined PEGs enhance their conjugation efficiency.

Example 3

Figure 6:
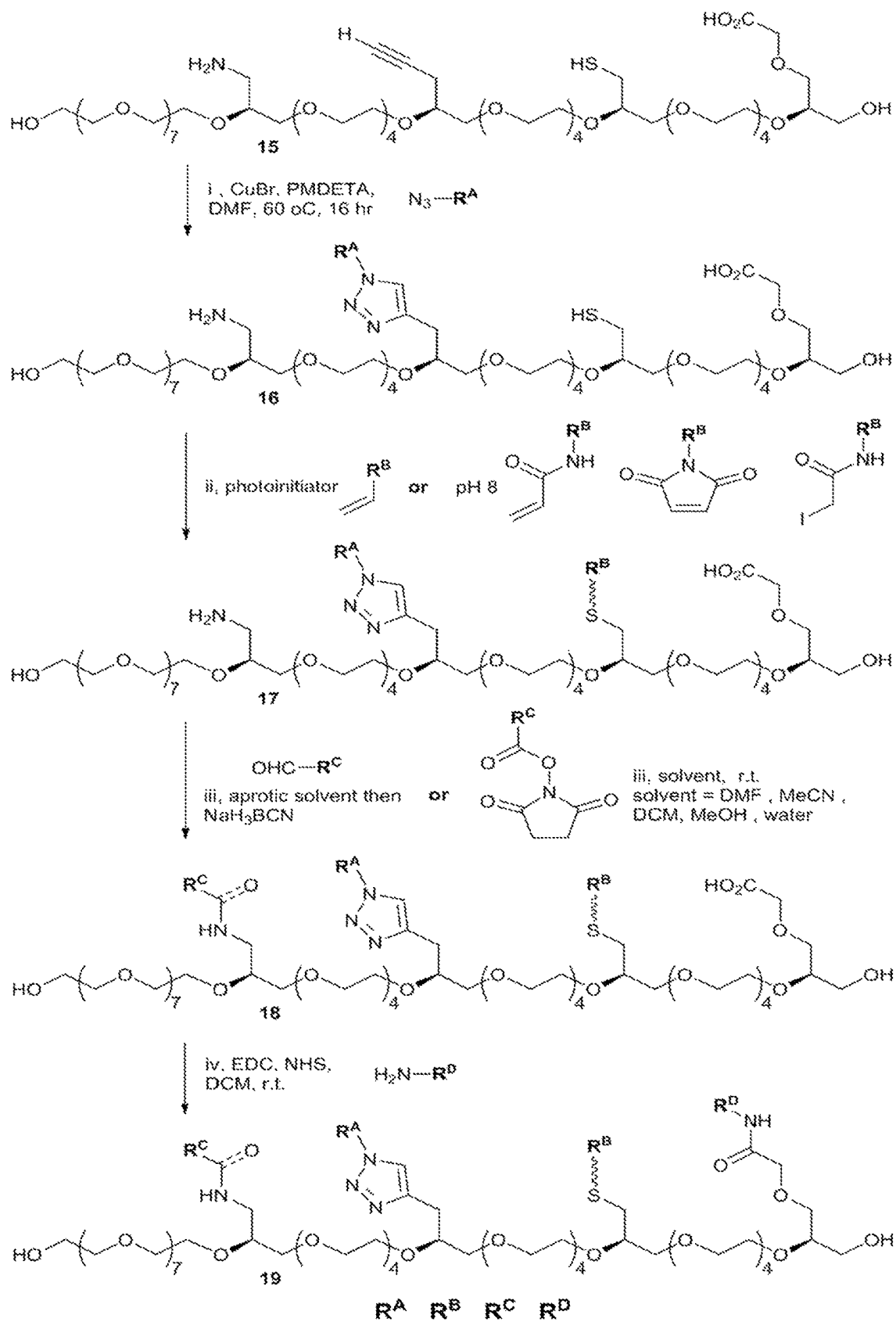
FIG. 6 shows the attachment of distinct side-chains ($R^{4'}$ $_{B,C,D}$) to defined monomer sequence PEG backbone portions comprising multiple distinct reactive side chain precursor groups.
Figure 8:
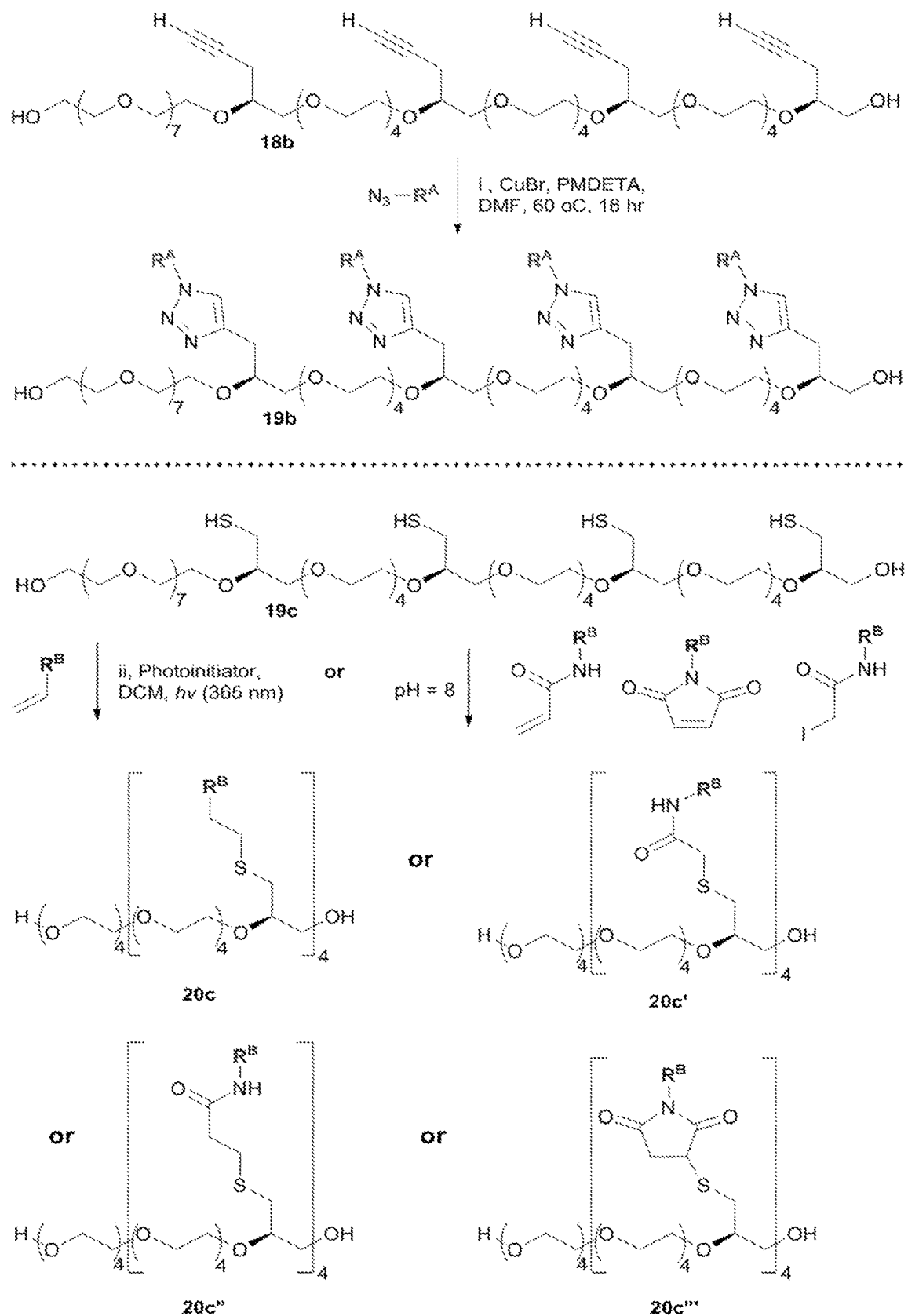
FIG. 8 shows the attachment by click chemistry of various side-chains to defined monomer sequence PEG backbone portions containing identical reactive side chain precursor groups.
Figure 10:
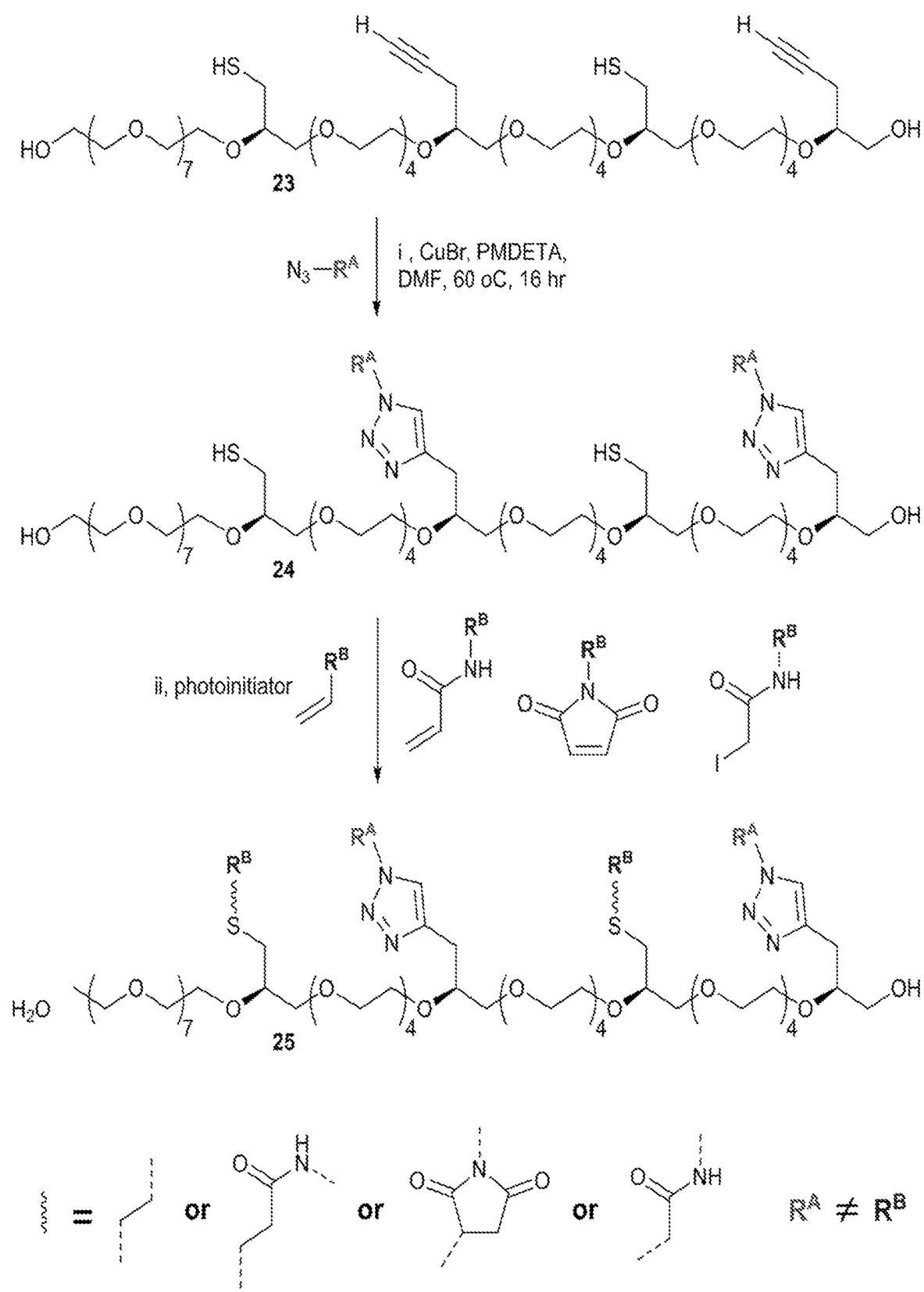
FIG. 10 shows the attachment by click chemistry of multiple distinct side-chains to PEG backbone portions containing multiple distinct reactive side chain precursor groups.
Figure 14:
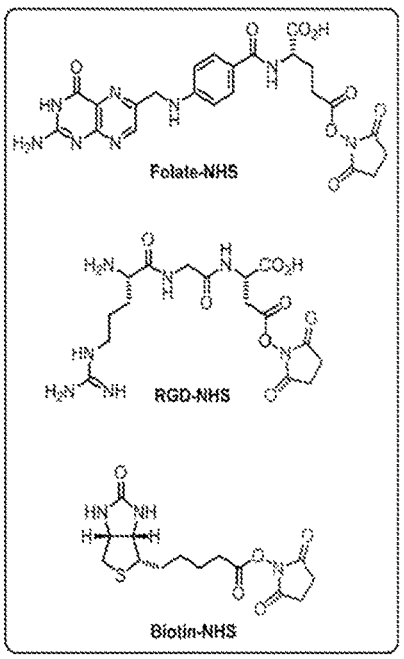
FIGS. 14 and 15 show various side chains suitable for use in the invention.
Figure 14:
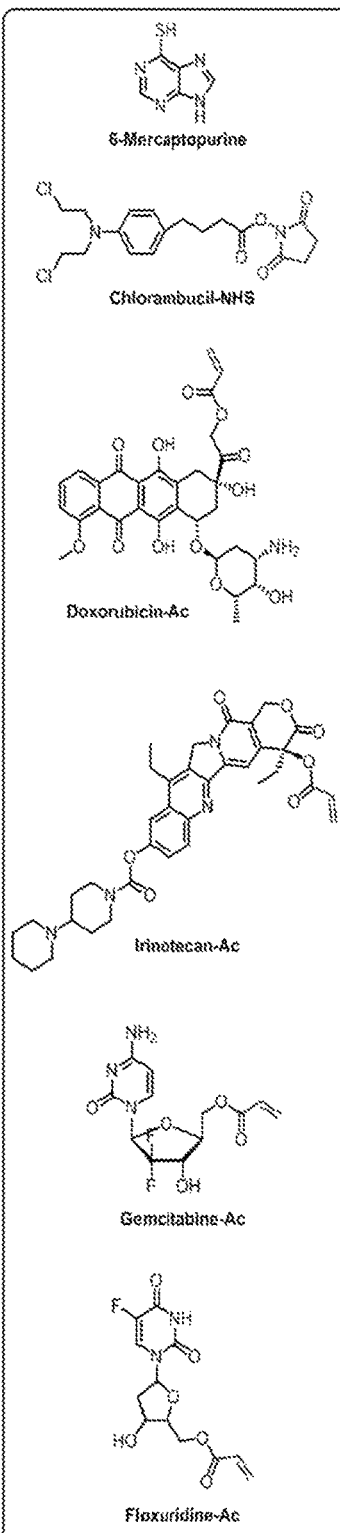
Figure 14:
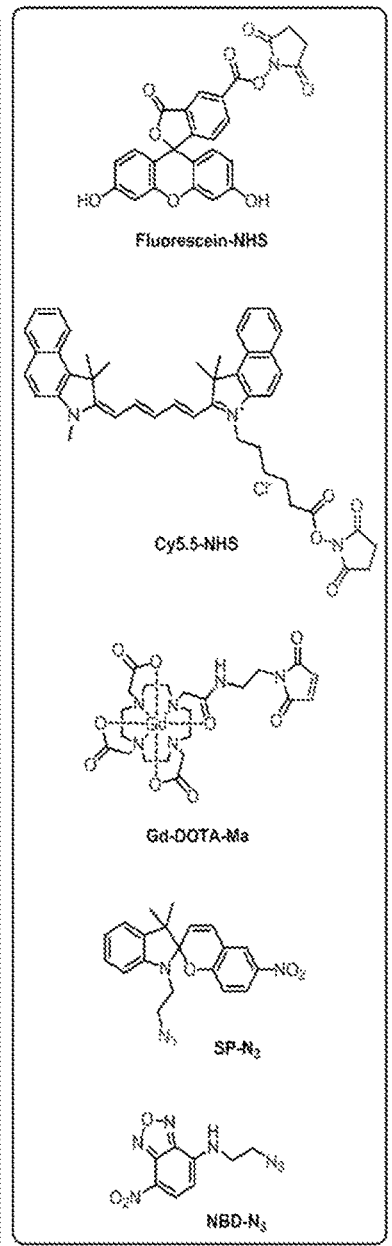
Figure 15:
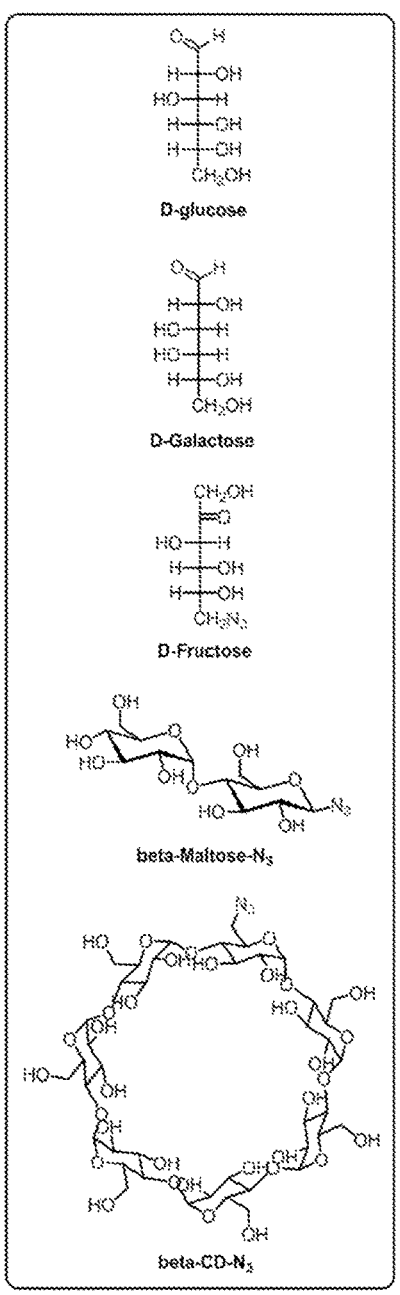
Figure 15:
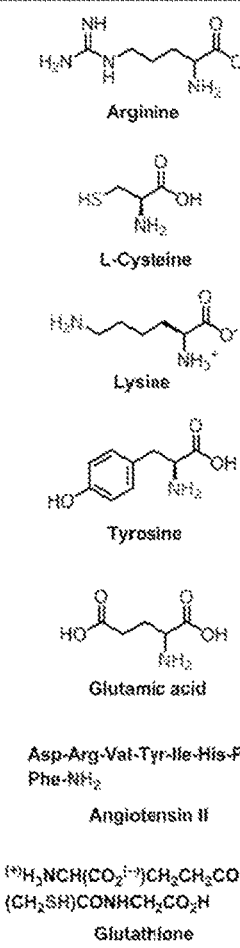
Figure 15:
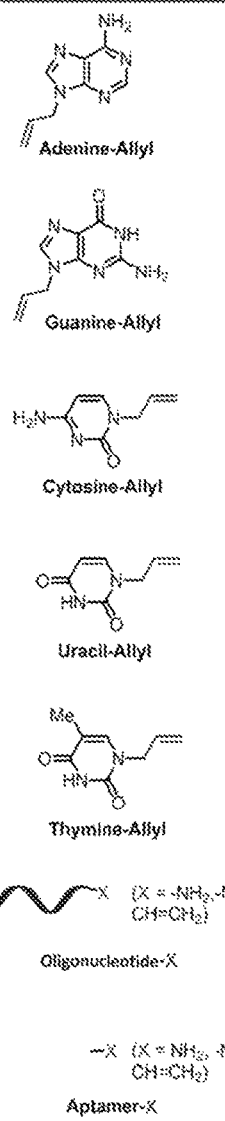
Figure 15:
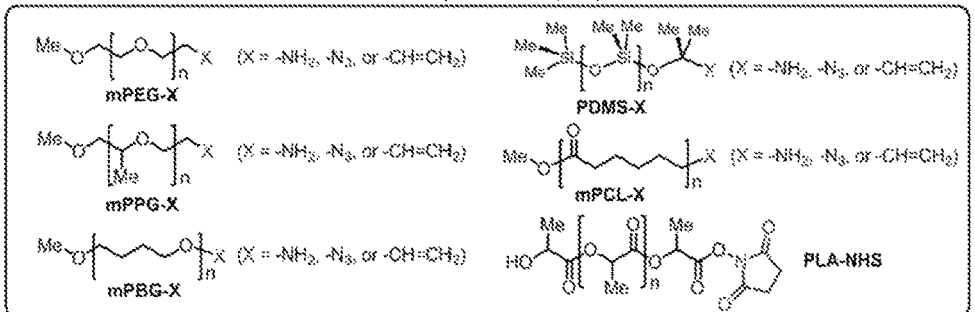

FIGS. 6, 8, and 10 show the post-modification process for the monodisperse sequence-defined backbone portion PEGs of Example 2. By using different conjugation approaches, diverse and distinct side-chains (see FIGS. 14 and 15) can be precision conjugated to specific reactive side chain precursor groups of the target PEGs to generate site-specific multifunctional PEGs with precision-guided side-chains. A range of potential functional side-chains are illustrated in FIGS. 14 and 15, including targeting molecules, drugs, imaging agents, sugars, amino acids, peptides, nucleobases, aptamers, oligonucleotides, and monodisperse synthetic polymers. In order to achieve effective conjugation to the target PEGs chains, particular side-chains are selectively coupled to reactive side chain precursor groups on the backbone portions, such as NHS-esters, —CH═CH$_2$, —N$_3$, —NH$_2$.

Figure 11:
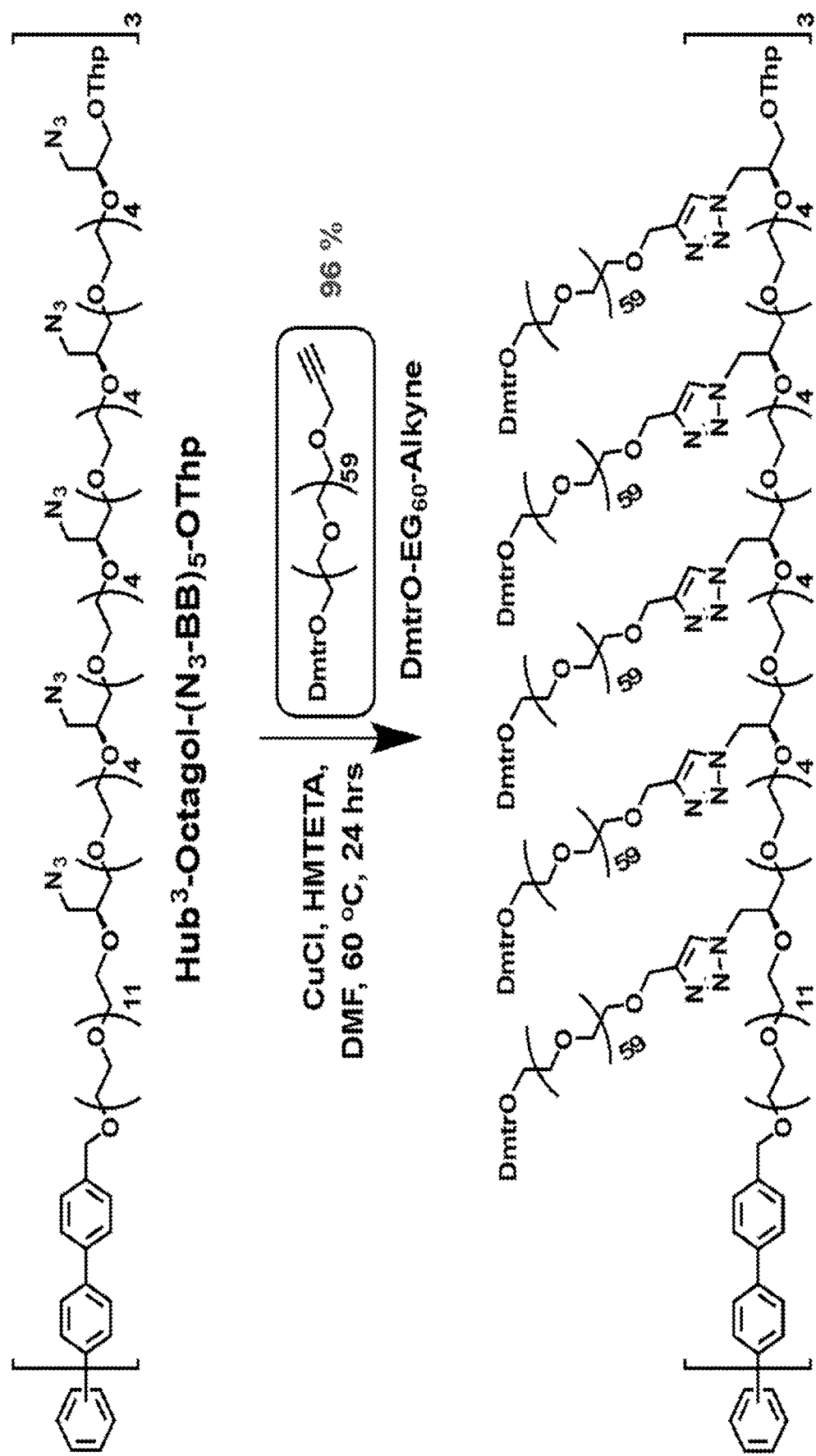
FIG. 11 shows the synthesis of a high-molecular-weight brush PEG homostar by click reaction between $Hub^3$-Octagol-($N_3$—BB)$_5$-OThp and DmtrO-$EG_{60}$-Alkyne.

FIG. 11 shows the post-modification process for a monodisperse azide-based PEG homostar (prepared according to Example 4 below). To provide efficient post modification, click chemistry was chosen to achieve efficient coupling between the alkyne group terminating the DmtrO-EG$_{60}$-Alkyne which is the side chain (SC) and the azide side chain precursor group on the Hub$^3$-Octagol-(N$_3$BB)$_5$-OThp. The click reaction between Hub$^3$-Octagol-(N$_3$—BB)$_5$-OThp and DmtrO-EG$_{60}$-Alkyne was carried out in DMF at 60 °C. using CuCl as catalyst and HMTETA as chelating agent. After 24 hrs, the target brush PEG homostar with large molecular weight was obtained with a high yield of >95%. At this stage, OSN diafiltration can be used to separate the Brush PEG Homostar from the DmtrO-EG$_{60}$-Alkyne.

Figure 12:
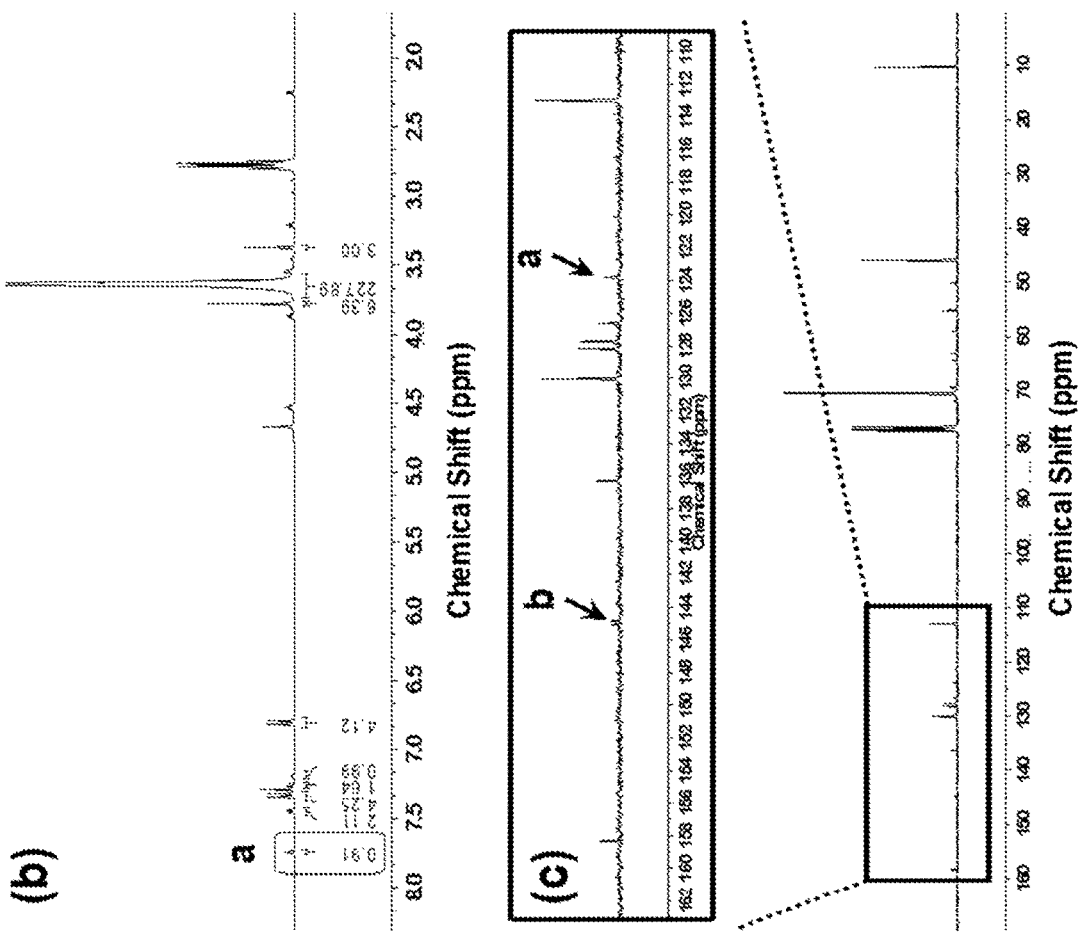
FIG. 12 shows (a) Click reaction between DmtrO-$EG_{12}$-Alkyne and PEG2k-$N_3$. (b) $^1H$ NMR and (c) $^{13}C$ NMR spectra of the target product DmtrO-$EG_{12}$-PEG2k.
Figure 12:
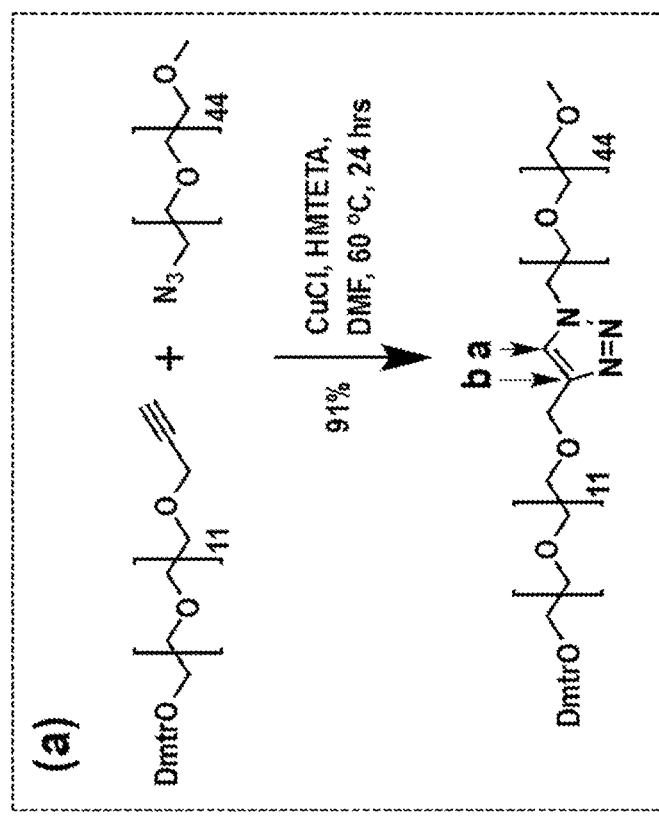

The feasibility of the click reaction illustrated in FIG. 11 is further exemplified in FIG. 12. The coupling between PEG 2000 with an azido end group (PEG2k-N$_3$) and DmtrO-EG12-Alkyne was performed to produce DmtrO-EG$_{12}$-PEG2k. After the click reaction between alkyne and azide groups, a characteristic triazole unit was formed. The new proton signal (a) and carbon signals (a and b) can been clearly observed in FIG. 12. Compared to other reaction types, click chemistry has several unique advantages including high selectivity, high coupling efficiency and mild reaction condition.

Figure 13:
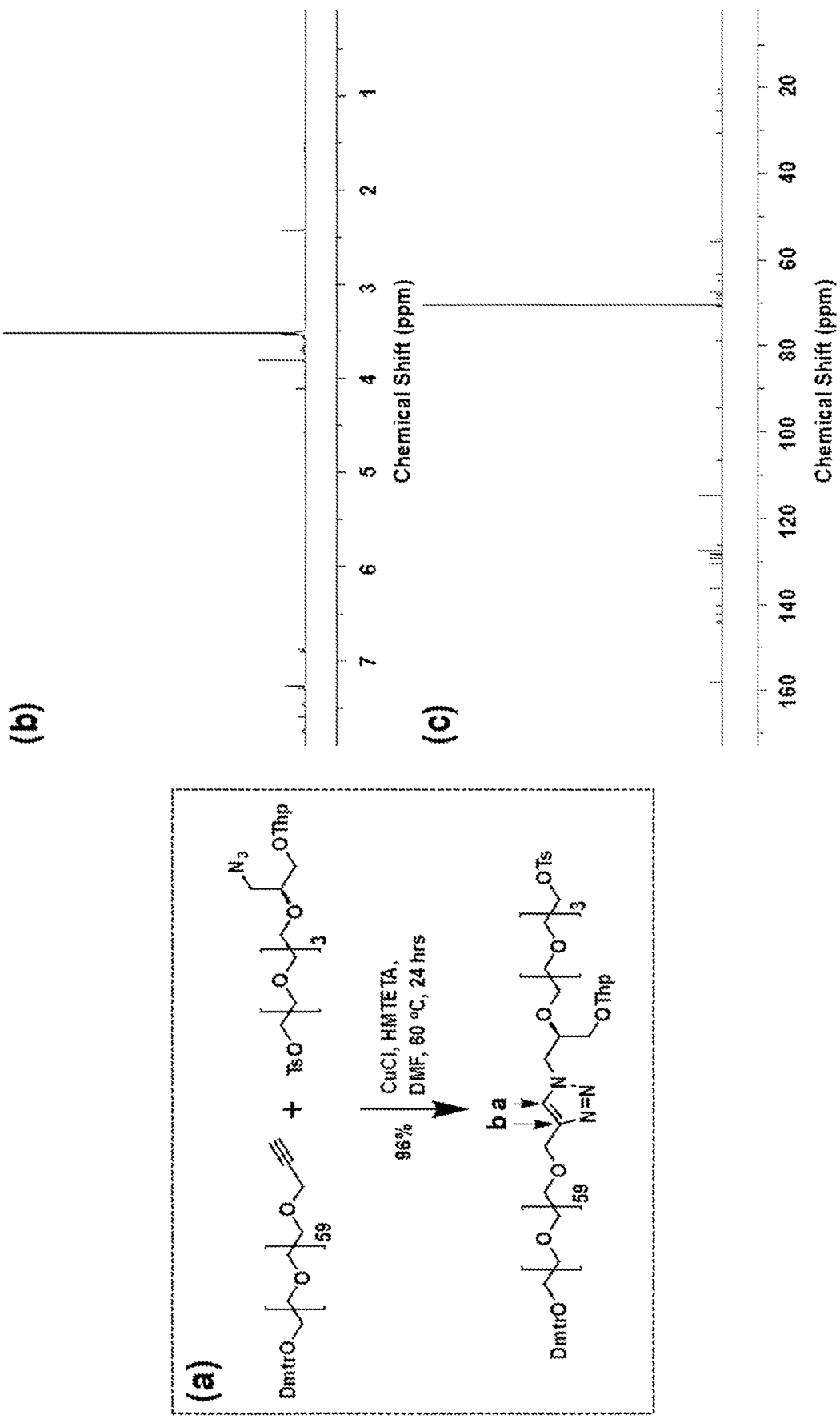
FIG. 13 shows (a) Click reaction between DmtrO-$EG_{60}$-Alkyne and $N_3$—BB. (b) $^1H$ NMR and (c) $^{13}C$ NMR spectra of the target product (DmtrO-$EG_{60}$-$N_3$—BB).

In a further demonstration, the azido building block (N$_3$—BB) was reacted with DmtrO-EG$_{60}$-Alkyne to generate the larger monomeric building block (DmtrO-EG$_{60}$-N$_3$—BB) under similar reaction conditions. After column purification, its chemical structure was confirmed using NMR spectroscopy (FIG. 13).

Example 4

Figure 16:
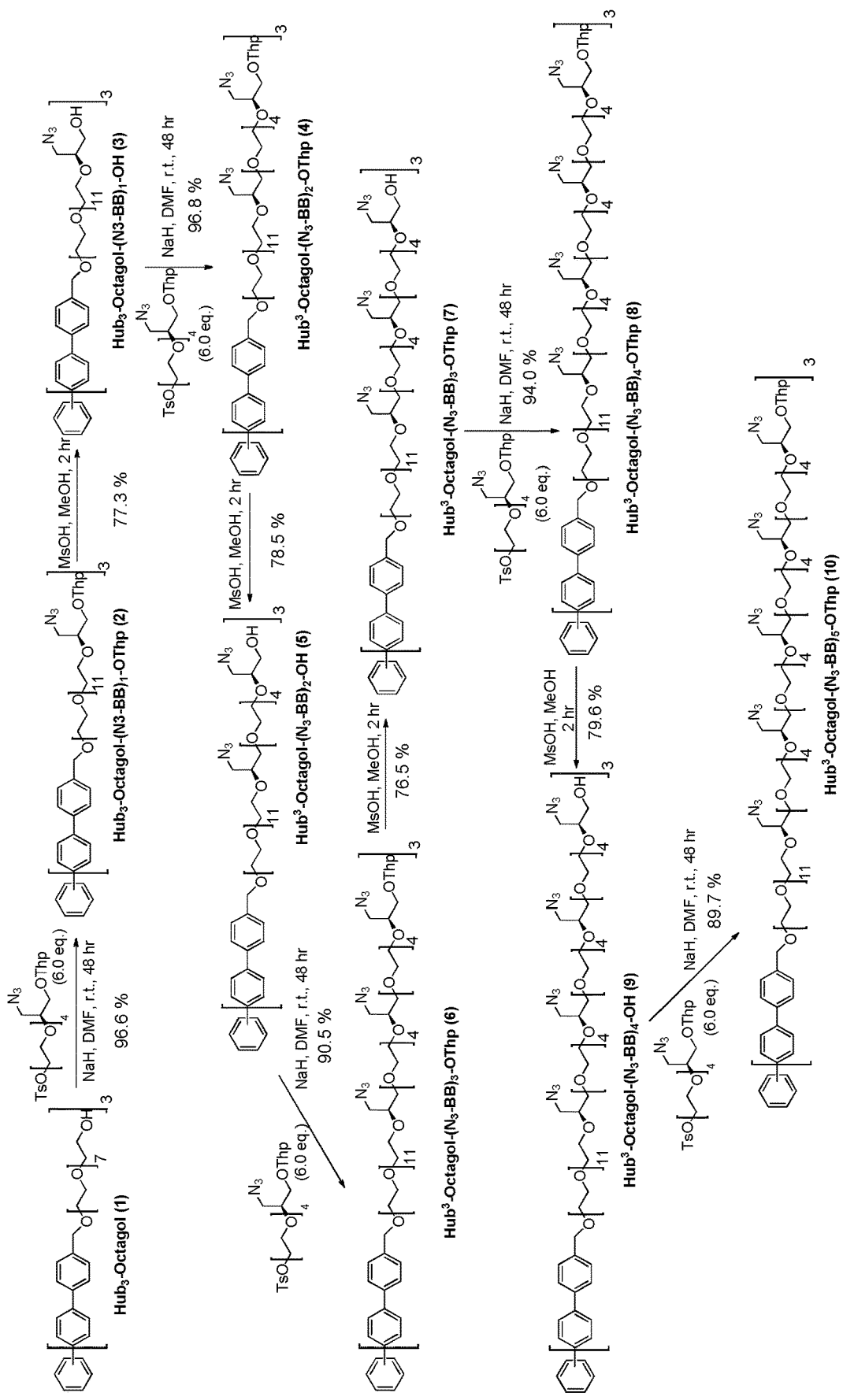
FIG. 16 shows the synthesis of $Hub^3$-Octagol-($N_3$—BB)$_5$-OThp involving 5 chain-extension and deprotection cycles.

FIG. 16 shows the coupling and deprotection processes used to form PEG homostar with N$_3$-based reactive side chain precursor groups. The monomeric N$_3$-building blocks obtained in FIG. 2 were coupled onto a synthesis support (Hub3-Octagol-OH) in any preselected order using column chromatography technology for purification during each round. After 5 coupling and deprotection cyles, the monodisperse PEG homostar (Hub$^3$-Octagol-(N$_3$—BB)$_5$-OThp) (ca. 65 mg) was obtained with a total yield of 26.4%, which contains 15 identical reactive azide groups (15 in FIG. 16). Thus, the azide-based PEG homostar is then ready for subsequent modification with a large range of side chains using highly efficient click chemistry, to further produce, for example, larger monodisperse PEG brush molecules.

Figure 17A:
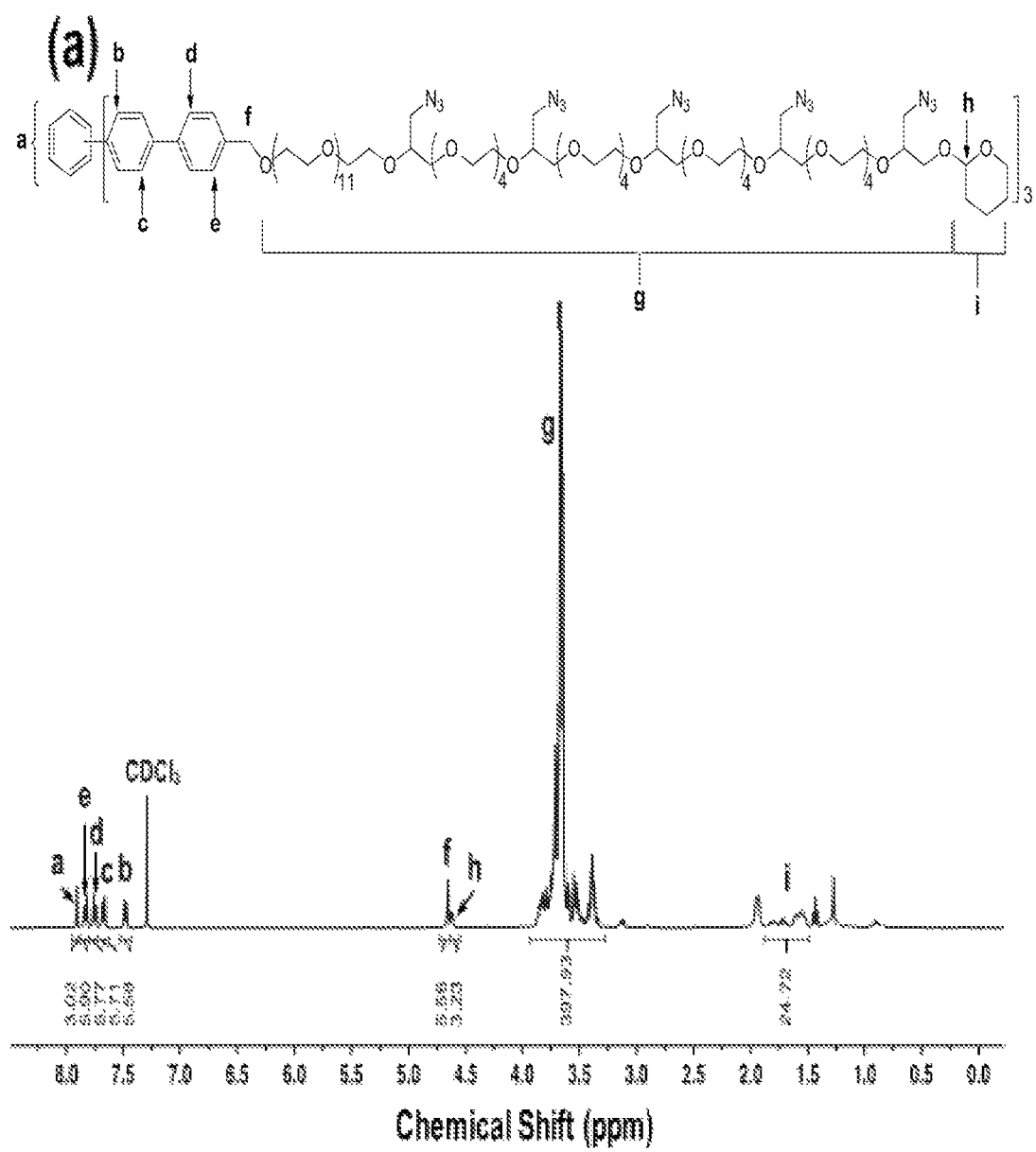
FIG. 17 shows (a) $^1H$ NMR and (b) $^{13}C$ NMR for the PEG homostar ($Hub^3$-Octagol-($N_3$—BB)$_5$-OThp) illustrated in FIG. 16.
Figure 17B:
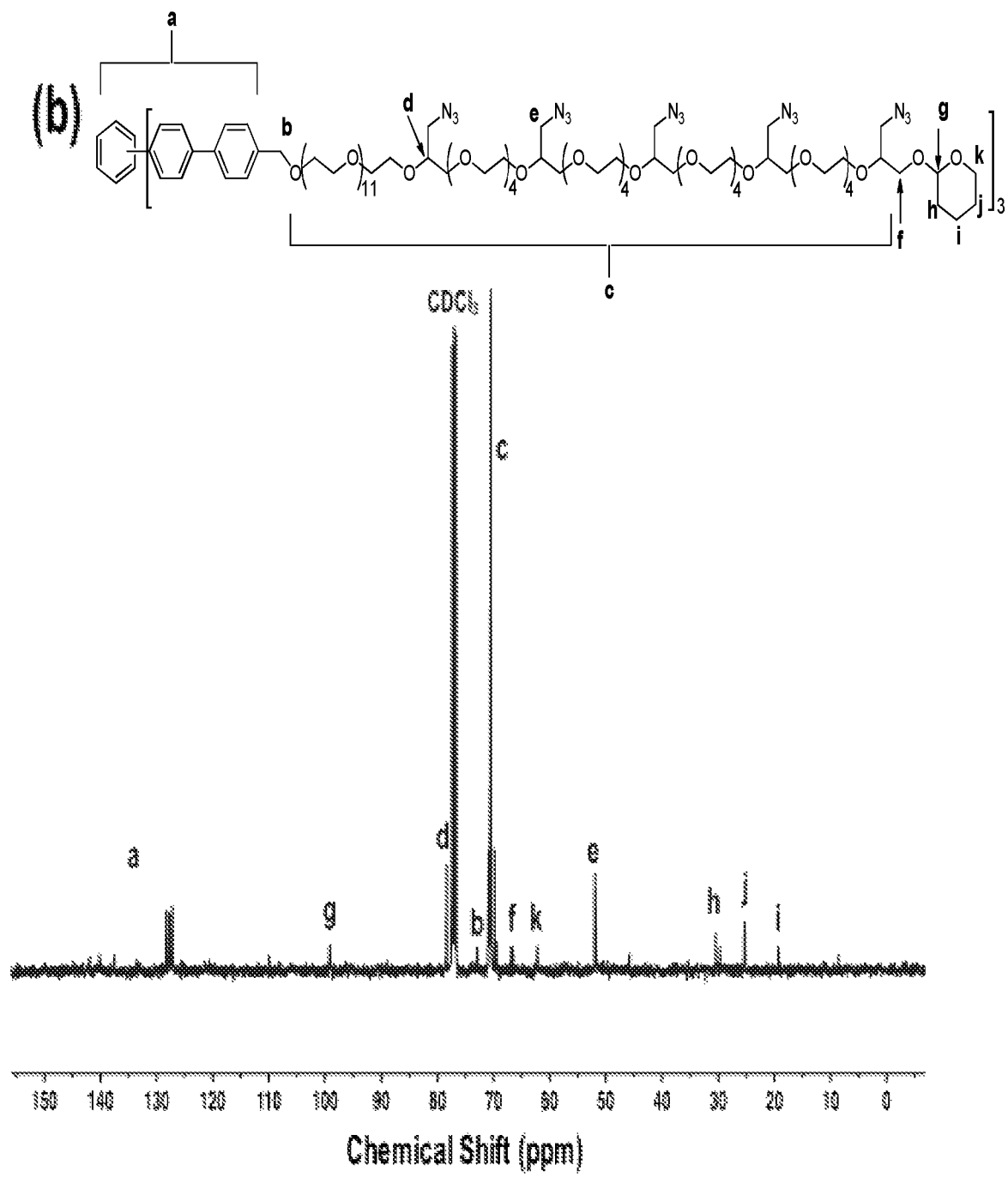
Figure 18:
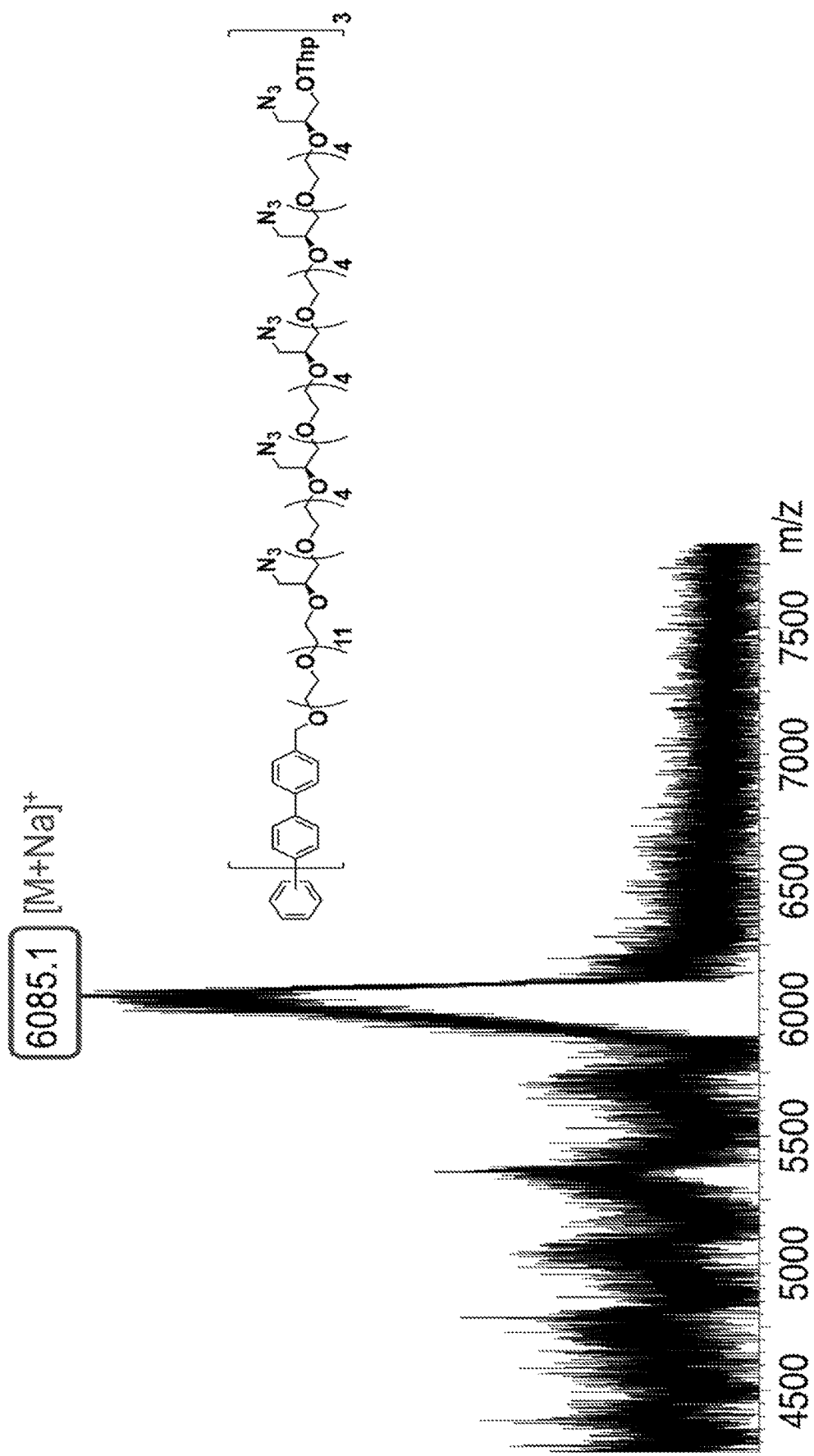
FIG. 18 shows the MALDI-TOF-MS spectrum for the PEG homostar ($Hub^3$-Octagol-($N_3$—BB)$_5$-OThp) illustrated in FIG. 16.

The chemical structure of the N$_3$-based PEG homostar (Hub$^3$-Octagol-(N$_3$—BB)$_5$-OThp) prepared as illustrated in FIG. 16 was confirmed by $^1$H NMR and $^{13}$C NMR spectroscopy (FIG. 17), and MALDI-TOF mass spectroscopy. Furthermore, the molecular weight was determined using MALDI-TOF-MS (FIG. 18), and its m/z peak at 6085.1 was clearly observed, which is consistent with its calculated molecular weight value.

Example 5

Example 5 demonstrates the feasibility of the diafiltration-based synthetic process of the invention. A laboratory scale cross-flow nanofiltration unit was used with 4 cross flow cells in series. Membrane discs of active area 14 cm$^2$ were used. An 80 mL feed tank was charged with a feed solution consisting of 0.04-0.07 g of BnO—BB (10), or N$_3$—BB (15), or Pmbs-BB (18) in MeOH, or 0.01-0.04 g Hub$^3$-Octagol in MeOH (see FIG. 2). The feed solution was re-circulated at a flow rate of 150 L h$^{-1}$ using a Micropump (GD series, Michael Smith Engineers Ltd., UK). A pressure of 20 bar in the cells was generated using a backpressure regulator which was located down-stream of a pressure gauge. During operation, permeate samples were collected from individual sampling ports for each cross-flow cell and the retentate sample was taken from the recycle line. Solvent flux was calculated as in Equation 1.

$$N_v = \frac{V}{At} \quad (1)$$

where V=volume of a liquid sample collected from the permeate stream from a specific cross-flow cell, t=time over which the liquid sample is collected, A=membrane area.

Membrane rejection $R_i$, was calculated as in Equation 2.

$$R_i = \left(1 - \frac{C_{Pi}}{C_{Ri}}\right) \times 100\% \quad (2)$$

where $C_{P,i}$=concentration of species i in the permeate (permeate being the liquid which has passed through the membrane), and $C_{R,i}$=concentration of species i in the retentate (retentate being the liquid which has not passed through the membrane).

The solute concentrations were measured using an Agilent HPLC machine. A reverse phase column (C4-300, 250 mm×4.6 mm, ACE Hichrom) was used and the mobile phases were MeOH and DI water buffered with 5 mM ammonium acetate. The HPLC pump flow rate was set at 1 ml min$^{-1}$ and the column temperature was set at 30° C.

Integrally skinned asymmetric PBI membranes were prepared by phase inversion as reported in Journal of Membrane Science 457 (2014) 62-72 using 18 to 19 wt % PBI dope solutions. Bench cast membranes were cast with the knife set at 250 μm and the casting machine set at a speed of 3.5 cm s$^{-1}$ (Elcometer, UK). Continuous cast membranes were cast with the knife set at 200 μm and a speed of 3 cm s$^{-1}$ (SepraTek, Korea). The PBI membranes were cross-linked using a,a'-dibromo-p-xylene in MeCN at 80° C. for 24 hours, followed by reaction with a polyetheramine conditioning agent (Jeffamine® 2005). Finally, the membrane surfaces were rinsed with IPA and the membranes were immersed in a solution of PEG400-IPA 1:1, stirring continuously for at least 4 hours, before drying.

Figure 19:
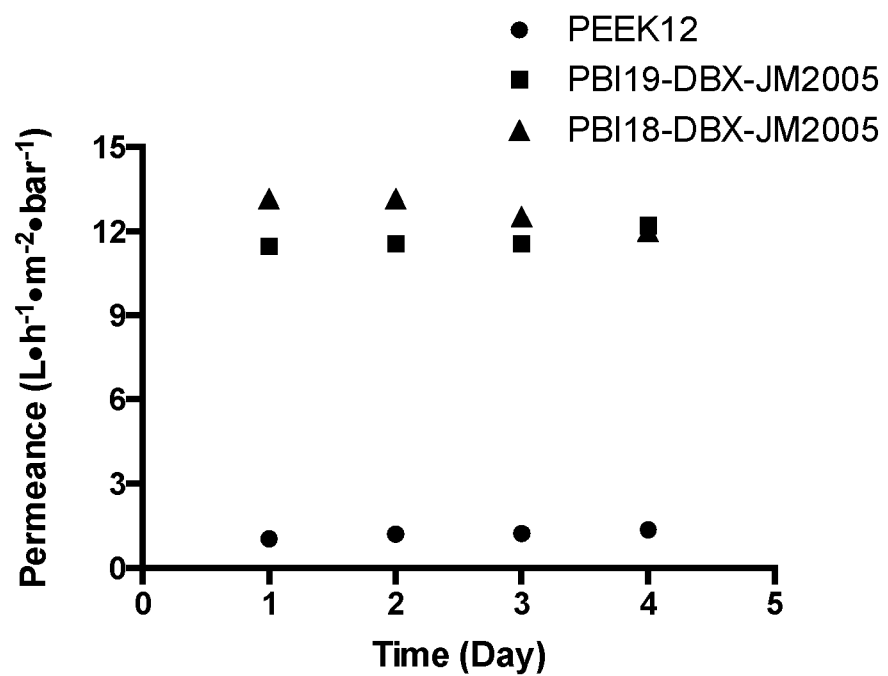
FIG. 19 shows the permeance (top) and rejection (bottom) of BnO—BB (10) in methanol using three different OSN membranes; PEEK membrane was cast as reported in Journal of Membrane Science 493(2015) 524-538, while bench cast PBI18-DBX-JM2005 and PBI19-DBX-JM2005 membranes were cast as described above.
Figure 19:
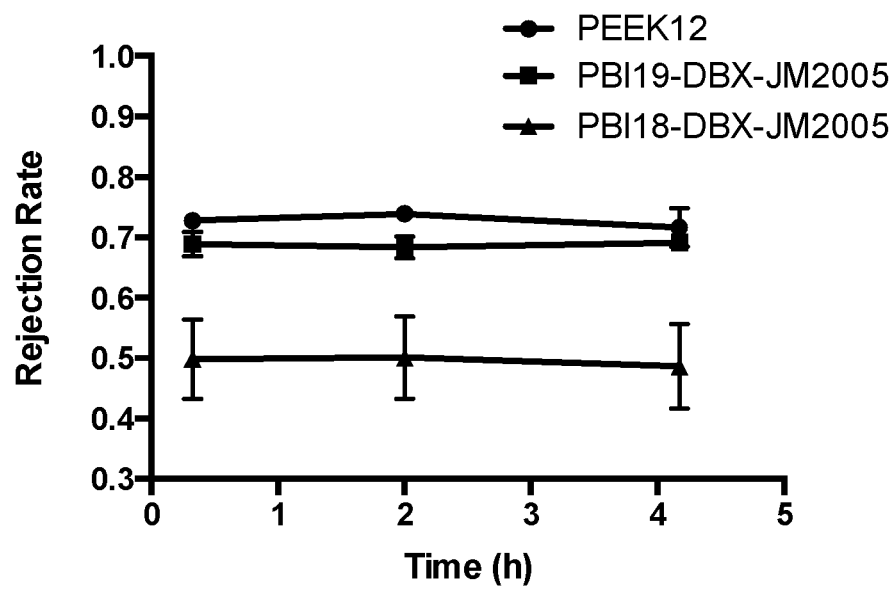
Figure 20:
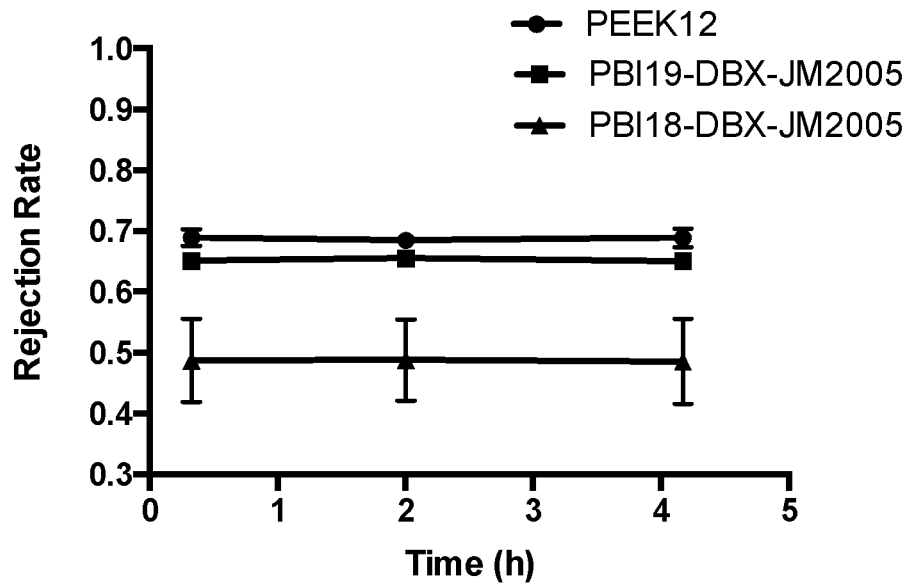
FIG. 20 shows the rejection of $N_3$—BB (15) in methanol (top) and the rejection of PmbS—BB (18) in methanol (bottom) using three different OSN membranes; PEEK membrane was cast as reported in Journal of Membrane Science 493(2015) 524-538, while bench cast PBI18-DBX-JM2005 and PBI19-DBX-JM2005 membranes were cast as described above.
Figure 20:
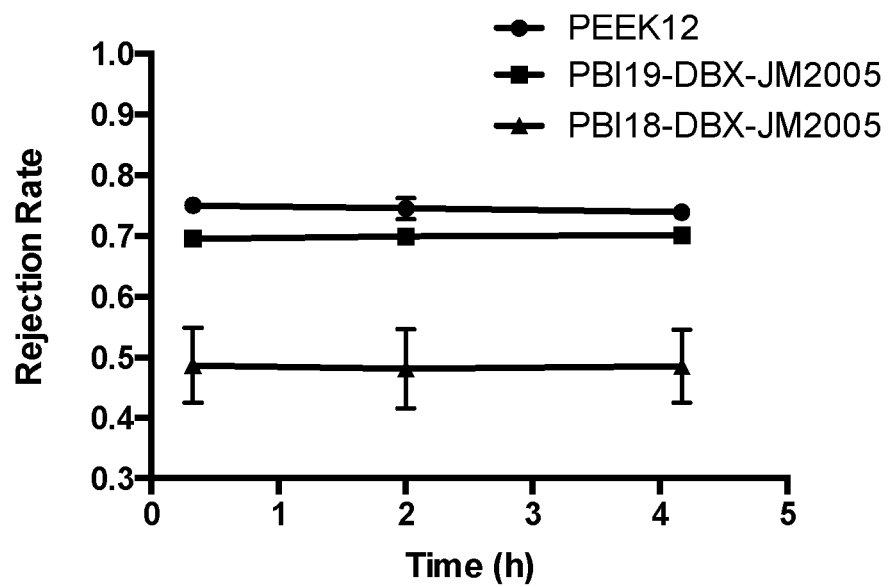

FIGS. 19-20 show the permeance and rejection of three different OSN membranes, using BnO—BB (10), N$_3$—BB (15), PmbS—BB (18) in MeOH. PEEK membrane was cast as reported in Journal of Membrane Science 493 (2015) 524-538 using a 12 wt % polymer dope solution and drying the membrane from acetone, while bench cast PBI18-DBX-JM2005 and PBI19-DBX-JM2005 membranes were cast as described above.

As is clear from FIGS. 19-20, PBI membranes have higher permeance than PEEK membranes. Furthermore, PBI19-DBX-JM2005 has higher rejection than PBI18-DBX-JM2005 for all building blocks tested.

Figure 21:
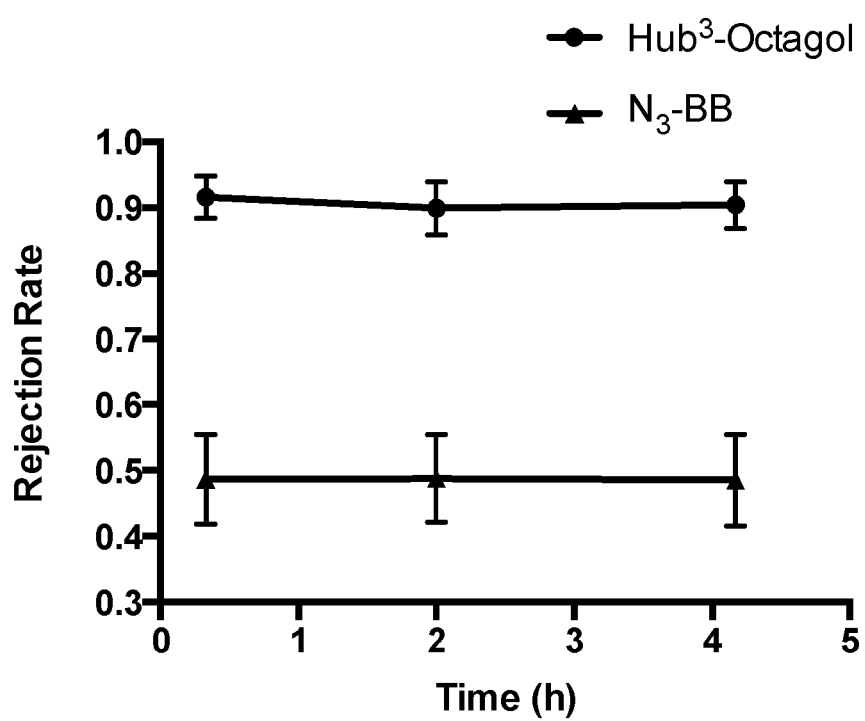
FIG. 21 shows the rejection of $N_3$—BB (15) and $Hub^3$-Octagol in methanol using PBI18-DBX-JM2005 membrane.

Continuously cast PBI18-DBX-JM2005 membranes were also tested for separation of Hub$^3$-Octagol from N$_3$—BB, as shown in FIG. 21 (having regard to the reaction described in FIG. 16). As shown in FIG. 21, the rejection of Hub$^3$-Octagol is significantly higher than the rejection of N$_3$—BB, showing that the main product (i.e. the growing homostar) can be easily purified from the building block via diafiltration. Moreover, the sequential attachment of building block units to Hub$^3$-octagol, for example to result in (Hub$^3$-Octagol-(N$_3$—BB)$_5$-OThp) from example 4, will necessarily increase the product size and therefore product rejection, thereby improving at the same time the membrane selectivity and process yield.

The preparation of the desired Brush PEG Homostar polymer on Hub$^3$ could be performed in at least two ways:

Method 1 following the present invention, the N$_3$—BB can be reacted with Hub$^3$-octagol to give Hub$^3$-octagol-EG$_4$ (N$_3$), and this can be repeated—with interspersed diafiltration to separate the growing polymer from the excess unreacted building block—to obtain the desired Hub$^3$-Octagol-(N$_3$—BB)5—OThp homostar with the desired monomer sequence including reactive side chain precursor groups; next, the reactive side chain precursor groups can be reacted with DmtrO-EG$_{60}$-Alkyne side chains; and then the resulting Brush-PEG-Homostar may be separated from residual EG$_{60}$ by diafiltration; or Method 2: following the state-of-the-art, Hub$^3$-octagol could be reacted directly with DmtrO-EG$_{60}$-N$_3$—BB (i.e. building blocks that have already been modified with the side chain), until the desired polymer length is obtained.

The two scenarios are characterized by different separation challenges:

Insofar as Method 1 is concerned, FIG. 21 illustrates that the Hub$^3$-octagol and N$_3$—BB have substantially different rejections using PBI18-DBX-JM2005, meaning that the growing homostar can be easily purified from the building block via diafiltration. Moreover, FIG. 22 (top) shows that the Hub$^3$-octagol and the DmtrO-EG$_{60}$-Alkyne side chain have substantially different rejections using PBI18-DBX-JM2005 (Ri>90% and Ri<60% respectively). This means that the finished homostar (decorated with reactive side chain precursor groups)—which will incidentally be more massive than the Hub$^3$-octagol starting material—can be reacted with the DmtrO-EG$_{60}$-Alkyne side chains, and the excess unreacted the DmtrO-EG$_{60}$-Alkyne side chains can then be separated from the Brush PEG homostar using diafiltration.

Figure 22:
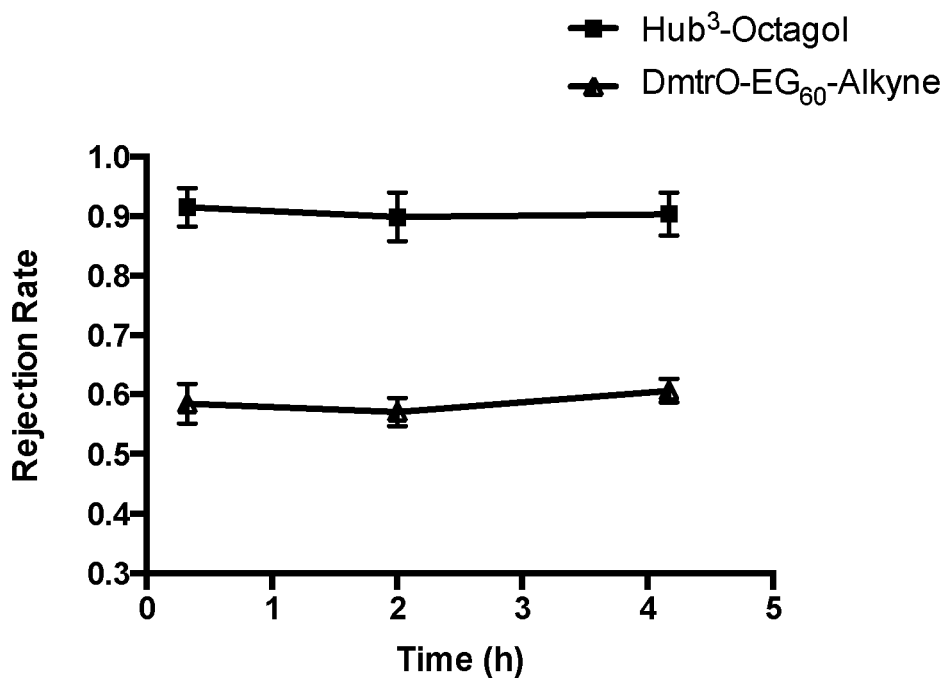
FIG. 22 (top) shows the rejection of $Hub^3$-Octagol and DmtrO-$EG_{60}$-Alkyne in methanol using PBI18-DBX-JM2005 membrane; and (bottom) the rejection of $Hub^3$-Octagol and DmtrO-$EG_{60}$-$N_3$—BB in methanol using PBI18-DBX-JM2005 membrane.
Figure 22:
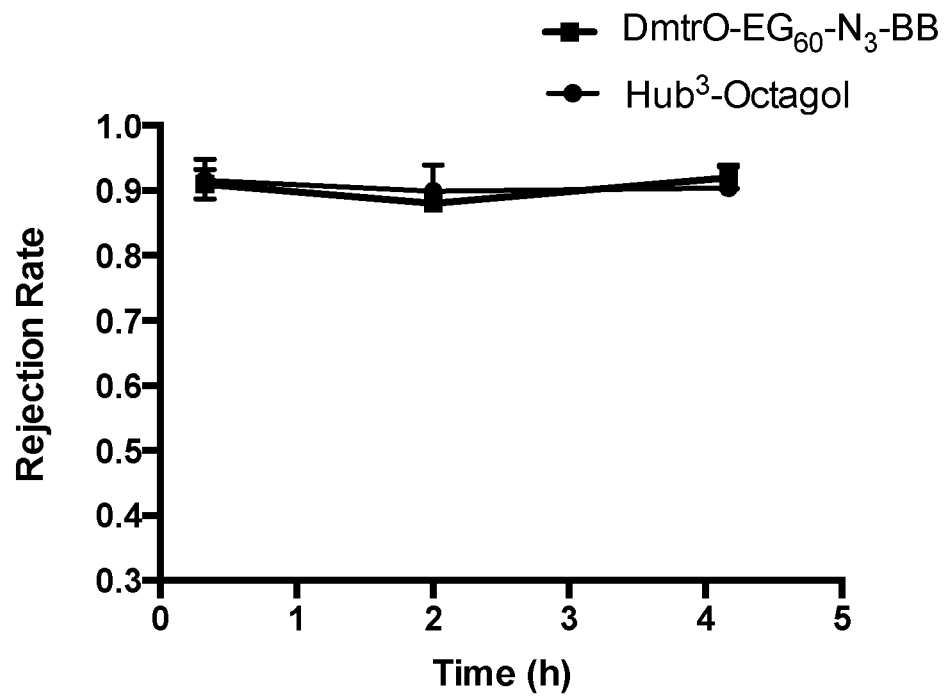

Insofar as Method 2 is concerned, FIG. 22 (bottom) shows that the Hub$^3$-octagol and the DmtrO-EG$_{60}$-N$_3$—BB (i.e. building blocks that have already been modified with the side chain) have highly similar rejections using PBI18-DBX-JM2005 (Ri>90%). As a consequence, the preparation of Brush PEG homostars by step-wise coupling of DmtrO-EG$_{60}$-N$_3$—BB to Hub$^3$-octagol with interspersed diafiltration purification steps is notably more difficult.

While specific embodiments of the invention have been described herein for the purpose of reference and illustration, various modifications will be apparent to a person skilled in the art without departing from the scope of the invention as defined by the appended claims.

The work leading to this invention has received funding from the [European Community's] Seventh Framework Programme ([FP7/2007-2013] under grant agreement n° 238291.

The invention claimed is:

1. A process for the preparation of a first compound being a defined monomer sequence polymer, in which at least two of the monomeric units are distinct from each other; the process comprising the steps of:
   i) synthesising a backbone portion of the first compound by performing one or more sequential monomeric coupling reactions in a first organic solvent, at least one of the monomeric units used in the sequential monomeric coupling reactions comprising a reactive side chain precursor group, such that the backbone portion comprises one or more reactive side chain precursor groups located at one or more predetermined positions along its length;
   ii) between each coupling reaction, separating a product of said one or more sequential coupling reactions from at least one second compound, which is a reaction by-product of the synthesis of the product and/or an excess of a reagent used for the synthesis of the product, and
   iii) attaching one or more side chains to the one or more reactive side chain precursor groups located along the length of the backbone portion;
   wherein during step (ii) the product of said one or more sequential coupling reactions and at least one second compound are dissolved in a second organic solvent and are separated by a process of diafiltration using a membrane that is stable in the organic solvent and which provides a rejection for the product which is greater than the rejection for the second compound.

2. The process of claim 1, wherein step (i) comprises synthesising a backbone portion comprising a first reactive side chain precursor group and a second reactive side chain precursor group, and step (iii) comprises attaching a first side chain to the first reactive side chain precursor group and a second side chain to the second reactive side chain precursor group.

3. The process of claim 2, wherein the first reactive side chain precursor group and the second reactive side chain precursor group are different, and the first side chain and the second side chain are different.

4. The process of claim 3, wherein a first monomeric unit used in the one or more sequential monomeric coupling reactions comprises the first reactive side chain precursor group and a second monomeric unit used in the one or more sequential monomeric coupling reactions comprises the second reactive side chain precursor group.

5. The process of claim 3, wherein the first reactive side chain precursor group is configured to react exclusively with the first side chain, and the second reactive side chain precursor group is configured to react exclusively with the second side chain.

6. The process of claim 1, wherein each side chain independently comprises a group selected from targeting molecules, active pharmaceutical ingredients, imaging agents, sugars, amino acids, peptides, nucleobases, aptamers, oligonucleotides, and monodisperse synthetic polymers.

7. The process of claim 1, wherein all of the monomeric units used in the one or more sequential monomeric coupling reactions of step (i) have identical backbone moieties.

8. The process of claim 1, wherein the backbone portion of the first compound is homopolymeric and is selected from poly(ethylene glycol) (PEG), poly(propylene glycol) (PPG), poly(butylene glycol), poly(ethylene oxide), poly(propylene oxide), poly(butylene oxide), poly(dimethylsiloxane) (PDMS), polybutadiene, polyisoprene, polystyrene, nylons and polyesters, poly(ethylene imines) (PEI), poly(propylene imines), poly(L-lysine) (PLL), poly(amidoamines) (PAA), poly(methyl methacrylate) (PMMA), poly(vinyl benzoic acid), poly(hydroxystyrene), N-substituted glycines, and poly(lactide-co-glycolide) (PLGA).

9. The process of claim 1, wherein the backbone portion of the first compound is a poly(ethylene glycol) homopolymer.

10. The process of claim 1, wherein not all of the monomeric units used in the one or more sequential monomeric coupling reactions of step (i) have identical backbone moieties.

11. The process of claim 10, wherein the backbone portion of the first compound is a copolymer formed from two or more of ethylene glycol, propylene glycol, butylene glycol, dimethylsiloxane, butadiene, isoprene, styrene, amides and esters, ethylene imines, propylene imines, L-lysine, amidoamines, methyl methacrylate, vinyl benzoic acid, hydroxystyrene, N-substituted glycines, lactide-co-glycolide, and polymers thereof.

12. The process of claim 1, wherein during synthesis of the first compound, the product is covalently attached to a synthesis support by an initial monomeric unit.

13. The process of claim 12, wherein the synthesis support is a branch point molecule having two or more reactive moieties capable of covalently binding to the initial monomeric unit.

14. The process of claim 1, wherein the one or more reactive side chain precursor groups each comprise a functional group.

15. The process of claim 14, wherein the functional group is selected from $-NH_2$, $-C\equiv C-$, $-SH$, $-CO_2H$, $-N_3$ and $-CH=CH_2$.

16. The process of claim 1, wherein the one or more sequential monomeric coupling reactions each comprise the steps of:
   a) reacting a starting material with an excess of an additional monomeric unit, the additional monomeric unit having one of its reactive terminal protected by a protecting group, and
   b) removing the protecting group so as to expose the reactive terminal such that it is ready for reaction with a subsequent additional monomeric unit,
   wherein the starting material is either an initial monomeric unit having at least one of its reactive terminals protected, or the polymeric product of the one or more sequential monomeric coupling reactions.

17. The process of claim 16, wherein the step (ii) is performed after step a) and again after step b).

* * * * *